(12) United States Patent
Khashman

(10) Patent No.: US 11,398,300 B2
(45) Date of Patent: Jul. 26, 2022

(54) MEDICAL DIAGNOSTIC PLATFORM

(71) Applicant: GROUNDBREAKING TECHNOLOGY LLC, Charlotte, NC (US)

(72) Inventor: Sam Faris Khashman, Charlotte, NC (US)

(73) Assignee: GROUNDBREAKING TECHNOLOGY LLC, Charlotte, NC (US)

( * ) Notice: Subject to any disclaimer, the term of this patent is extended or adjusted under 35 U.S.C. 154(b) by 228 days.

(21) Appl. No.: 15/892,099

(22) Filed: Feb. 8, 2018

(65) Prior Publication Data

US 2018/0226143 A1 Aug. 9, 2018

Related U.S. Application Data

(60) Provisional application No. 62/456,395, filed on Feb. 8, 2017.

(51) Int. Cl.
| | |
|---|---|
| *G16H 10/60* | (2018.01) |
| *G06F 16/174* | (2019.01) |
| *G06F 16/25* | (2019.01) |
| *G16H 50/70* | (2018.01) |
| *G16H 50/20* | (2018.01) |
| *G06F 11/30* | (2006.01) |

(52) U.S. Cl.
CPC ......... *G16H 10/60* (2018.01); *G06F 11/3006* (2013.01); *G06F 11/3051* (2013.01); *G06F 16/174* (2019.01); *G06F 16/254* (2019.01); *G16H 50/20* (2018.01); *G16H 50/70* (2018.01)

(58) Field of Classification Search
CPC ........ G16H 10/60; G16H 50/70; G16H 50/20; G06F 16/174; G06F 16/254; G06F 11/3006
See application file for complete search history.

(56) References Cited

U.S. PATENT DOCUMENTS

| | | | |
|---|---|---|---|
| 8,468,244 B2 * | 6/2013 | Redlich ................ | G06Q 10/107 709/225 |
| 2015/0213225 A1* | 7/2015 | Amarasingham ....... | G06F 19/00 705/2 |

OTHER PUBLICATIONS

Mark Kasunic, Improving Data Quality Through Anomaly Detection, Software Engineering Institute Blog (Jul. 2011) (Year: 2011).*

(Continued)

*Primary Examiner* — Evangeline Barr
*Assistant Examiner* — Jordan L Jackson
(74) *Attorney, Agent, or Firm* — Moore & Van Allen PLLC; Nicholas C. Russell; Vaidehi Bachoti

(57) ABSTRACT

Embodiments of the invention are directed to a system, method, or computer program product for a medical diagnostic platform. The system accesses data collected on one or more source server systems and selectively extracts user information according to the desired criteria of an operator or user. The system generates a secure, user database, wherein the user database comprises the selectively extracted user information, such as medical, financial, and demographic information, from multiple source server systems creating a centralized database of user information stored in a single location. The system further generates a medical diagnostic analysis of the user in comparison to similar users and displays recommended and extrapolated results for diagnoses, procedures, treatments, and costs for the user based on the history of the similar users.

20 Claims, 12 Drawing Sheets

(56) References Cited

OTHER PUBLICATIONS

Scholte et at., Data extraction from electronic health records (EHRs) for quality measurement of the physical therapy process: comparison between EHR data and survey data, 16:141 BMC Medical Informatics and Decision Making (2016) (Year: 2016).*

Peter Feiler and Jörgen Hansson, Flow Latency Analysis with the Architecture Analysis and Design Language (AADL), Software Engineering Institute (Dec. 2007) (Year: 2007).*

Iliya Grigorik, High Performance Browser Networking, Oreilly (2013)(available at https://www.oreilly.com/library/view/high-performance-browser/9781449344757/ch01.html) (Year: 2013).*

Marcel Cavalcanti de Castro, Enhancing P2P Systems over Wireless Mesh Networks, Dissertation Karlstad University Studies 1-60 (Year: 2011).*

Welton et al., Improving I/O Forwarding Throughput with Data Compression, IEEE International Conference on Cluster Computing (Sep. 2011) (Year: 2011).*

Mark Kasunic, Improving Data Quality Through Anomaly Detection, Software Engineering Institute Blog (Jul. 2011) (Year: 2011).*

William Landi and R. Bharat Rao, Secure De-identification and Re-identification, AMIA Symposium Proceedings 905 (Year: 2003).*

\* cited by examiner

MEDICAL DIAGNOSTIC PLATFORM

RELATED APPLICATIONS AND PRIORITY CLAIM 35 U.S.C. § 119

This application is a non-provisional filing of U.S. Provisional Application No. 62/456,395, filed Feb. 8, 2017, the contents of which are hereby incorporated by reference herein.

BACKGROUND

Entities in the field of medicine and healthcare, such as hospitals and insurance carriers typically store and maintain a wealth of medical, financial, and demographic information associated with patients and customers in multiple disparate databases. The data in these disparate databases may potentially prove useful to other individuals who might wish to compare their own medical history to that of a collection of similar individuals in order to glean potential diagnoses, procedures, treatments, and associated costs that might become necessary in the future. However, effectively accessing and extracting this data is possible by conventional methods, if at all, by using time consuming and labor intensive approaches. Therefore, there exists a need for an innovative method for efficiently extracting, collecting, and correlating patient medical, financial, and demographic information for medical diagnostics and predictive analysis/analytics.

BRIEF SUMMARY

The following presents a simplified summary of one or more embodiments of the invention in order to provide a basic understanding of such embodiments. This summary is not an extensive overview of all contemplated embodiments, and is intended to neither identify key or critical elements of all embodiments, nor delineate the scope of any or all embodiments. Its sole purpose is to present some concepts of one or more embodiments in a simplified form as a prelude to the more detailed description that is presented later.

Embodiments of the present invention address these and/or other needs by providing an innovative system, method, and computer program product for selective data extraction and user correlation. Embodiments of the invention are directed to a system for resource-efficient extraction and optimized transmission of medical data, the system comprising: at least one memory device with computer-readable program code stored thereon; at least one communication device connected to a network; at least one processing device operatively coupled to the at least one memory device and the at least one communication device, wherein the processing device is configured to execute the computer-readable program code to: establish an operative communication channel with a source server system, the source server system comprising source data and source user information; preprocess at least a portion of the source data and the source user information on the source server system; extract, selectively, the portion of the source data and the source user information from the source server system to a target server system, wherein the portion of the source data and the source user information comprises information associated with one or more users; and generate a user database on the target server system, wherein the user database comprises the portion of the source data and the source user information selectively extracted from the source server system.

In some embodiments, the system further comprises a data extraction device installed on the source server system, wherein the data extraction device utilizes computing resources of the source server system to preprocess and selectively extract the portion of the source data and the source user information.

In some embodiments, the at least one processing device is further configured to: determine one or more latent computing resources of the source server system; and based on determining the one or more available technical resources, initiate extraction of the source data from the source server system to the target server system, wherein the one or more latent computing resources are utilized to process and extract the portion of the source data and the source information.

In some embodiments, the one or more latent computing resources of the source server system further comprise a plurality of decentralized computing resources of one or more computing devices associated with the source server system.

In some embodiments, the at least one processor is further configured to selectively extract the portion of the source data and the source user information periodically at a predetermined time.

In some embodiments, preprocessing the portion of the source data and the source user information on the source server system the system normalizes, delimits, and de-identifies the data using latent computing resources of the source server system prior to extraction of the data from the source server system.

In some embodiments, the portion of the source data and the source user information comprises a first file size, and wherein the at least one processing device is further configured to: generate an encoded data file having a second file size from the portion of the source data and the source user information, wherein the second file size is less than the first file size; and transmit the encoded data file to the target server system.

In some embodiments, the at least one processing device is further configured to install an extraction script on the source server system to preprocess and selectively extract the portion of the source data and the source user information on the source server system.

In some embodiments, selectively extracting the portion of the source data and the source information further comprises: receiving at least one data descriptor input from a user interface; based on the at least one data descriptor, identifying pertinent data for extraction from the portion of the source data and the source user information; stripping the portion of the source data and the source user information based on the at least one data descriptor to construct a pertinent data file, the pertinent data file comprising only the pertinent data; and extracting the pertinent data file from the source server system.

Embodiments of the invention are further directed to a computer-implemented method for resource-efficient processing and selective extraction of medical data, the method comprising: establishing an operative communication channel with a source server system comprising source data and source user information; preprocessing at least a portion of the source data and the source user information on the source server system, wherein preprocessing comprises at least one of normalizing, de-identifying, and delimiting the portion of the source data and the source user information; extracting, selectively, the portion of the source data and the source user information from the source server system to a target server system, wherein the portion of the source data and the source user information comprises information associated with one or more users; and generating a user database on the target server system, wherein the user database comprises the portion of the source data and the source user information extracted from the source server system.

In some embodiments, normalizing the portion of the source data and the source user information further comprises: identifying one or more anomalies and redundancies in the portion of the source data and the source user information, wherein the one or more anomalies and redundancies comprise missing data, incomplete data, inconsistent data, incorrect data, unformatted data, and repeated data entries; and based on identifying the one or more anomalies and redundancies, stripping the one or more anomalies and redundancies from the portion of the source data and the source user information prior to extraction.

In some embodiments, de-identifying the portion of the source data and the source user information further comprises: identifying at least some personal identifying information within the portion of the source data and the source user information; and based on identifying the at least some personal identifying information, stripping the portion of the source data and the source user information of the personal identifying information to generate de-identified data.

In some embodiments, generating the de-identified data further comprises constructing at least one tracer for each de-identified data record, wherein the at least one tracer is a unique identifier for the de-identified data record configured for tracking and monitoring of the de-identified data record during data extraction, and wherein the at least one tracer is used for reconstruction of the portion of the source data and the source user information at the target server system.

In some embodiments, delimiting the portion of the source data and the source user information further comprises: generating encoded source data by inserting the at least one tracer into the portion of the source data and the source user information; and generating an encoded data file comprising the encoded source data.

In some embodiments, generating the encoded source data further comprises inserting a delimiter into the encoded source data with the tracer and the portion of the source data and the source user information.

In some embodiments, selectively extracting the portion of the source data and the source information further comprises: receiving at least one data descriptor input from a user interface; based on the at least one data descriptor, identifying pertinent data for extraction from the portion of the source data and the source user information; stripping the portion of the source data and the source user information based on the at least one data descriptor, wherein a pertinent data file comprising only the pertinent data is created; and selectively extracting the pertinent data file from the source server system.

In some embodiments, the computer-implemented method further comprises selecting a first communication channel having a first bandwidth and a first data transfer rate for transfer of the portion of the source data and the source user information; determining that the first communication channel is unavailable; in response to determining that the first communication channel is unavailable, selecting a second communication channel having a second bandwidth and a second data transfer rate for transfer of the portion of the source data and the source user information, wherein at least one of the second bandwidth and the second data transfer rate are less than the first bandwidth and the first data transfer rate; and transferring the portion of the source data and the source user information to the target server system via the second communication channel.

Embodiments of the invention are further directed to a medical diagnostic platform comprising at least one non-transitory computer-readable medium having computer-readable program code portions embodied therein, the computer-readable program code portions comprising: a first executable portion configured for generating a centralized user database, wherein the centralized user database comprises anonymized user data selectively extracted from a plurality of source server systems via one or more operative communication channels; a second executable portion configured for receiving, via a user interface, at least one descriptor from a user; a third executable portion configured for, based on the at least one descriptor received from the user, matching the user to one or more similar users associated with the anonymized user data; a fourth executable portion configured for retrieving tailored data from the centralized user databased associated with the one or more similar users; and a fifth executable portion configured for generating a medical diagnostic report comprising the tailored data, wherein the medical diagnostic report is presented to the user via the user interface.

In some embodiments, the medical diagnostic report comprises at least one of extrapolated diagnoses, treatments, procedures, and costs associated with the user based on the similar users and the anonymized user data.

In some embodiments, the at least one descriptor is selected from a group comprising age, gender, ethnicity, geographic location, income, diagnoses, symptoms, procedures, treatments, and drug prescriptions associated with the user or the similar users.

The features, functions, and advantages that have been discussed may be achieved independently in various embodiments of the present invention or may be combined with yet other embodiments, further details of which can be seen with reference to the following description and drawings.

BRIEF DESCRIPTION OF THE DRAWINGS

Figure 1:
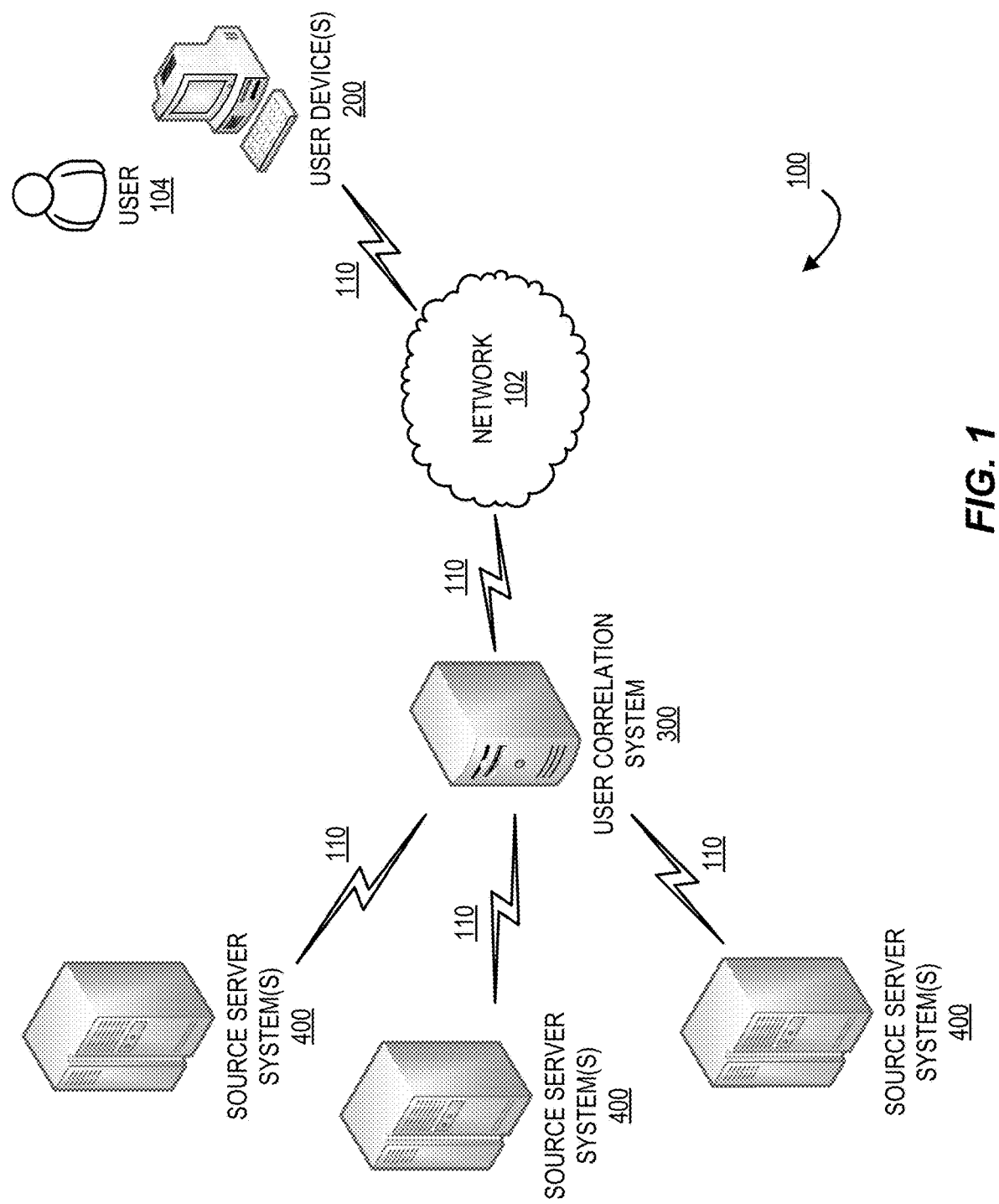
Figure 2:
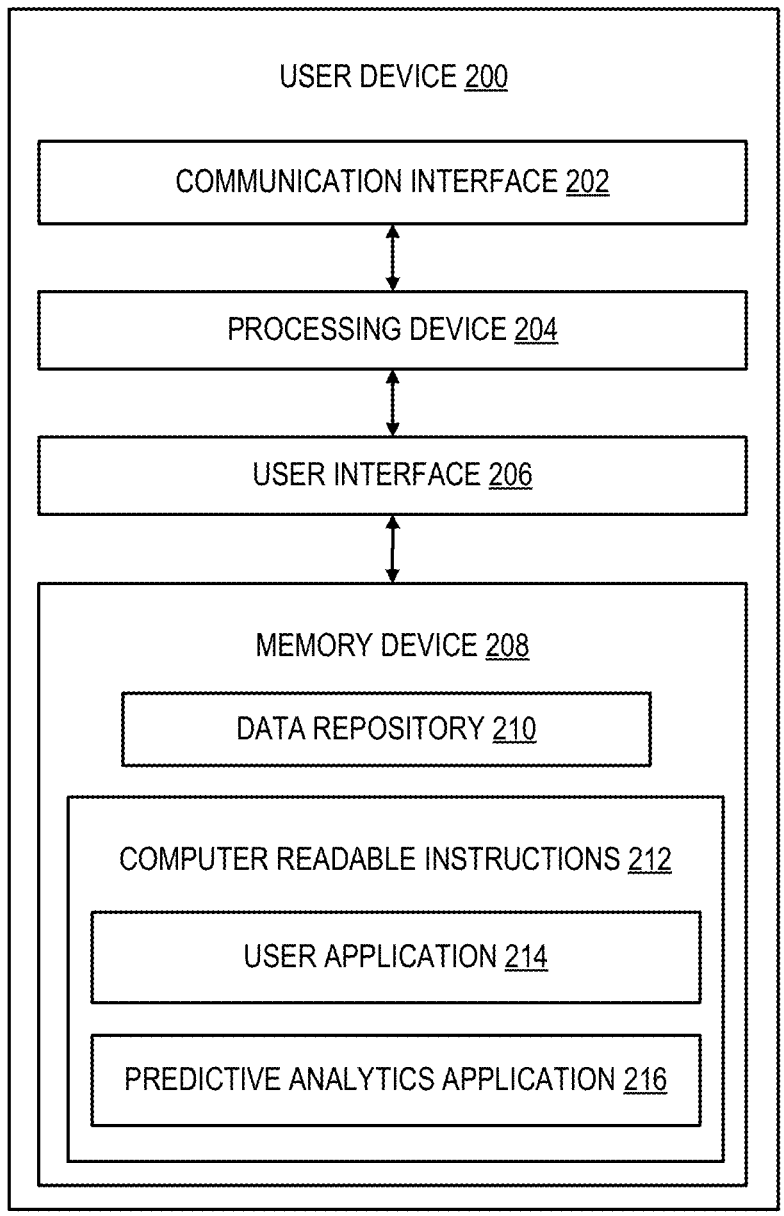
Figure 3:
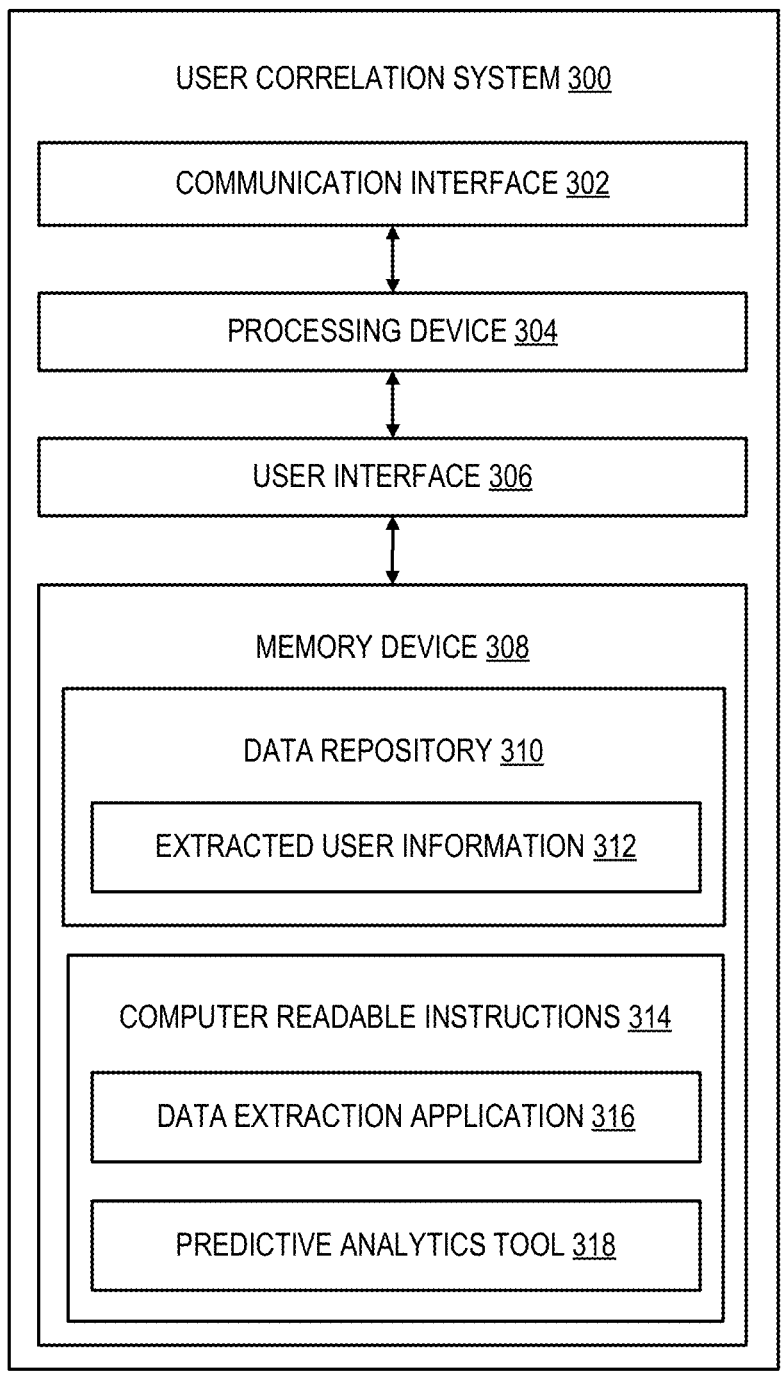
Figure 4:
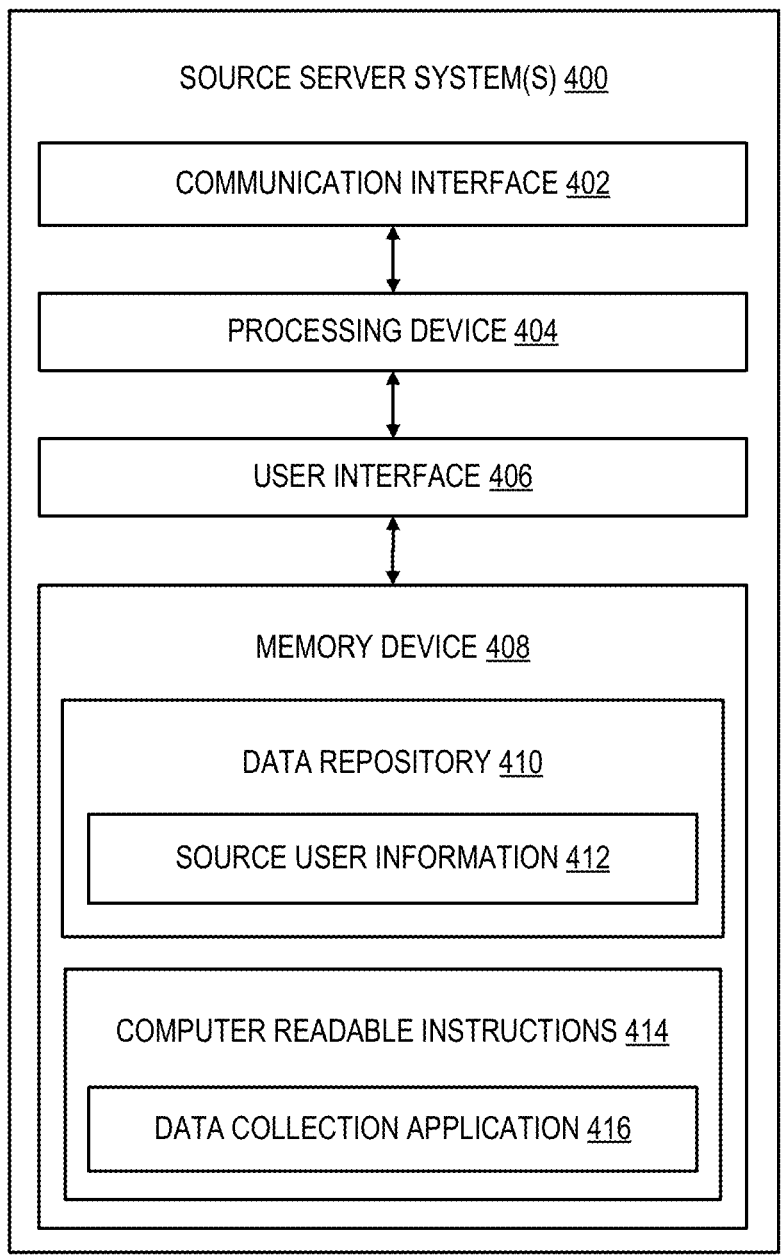
Figure 5:
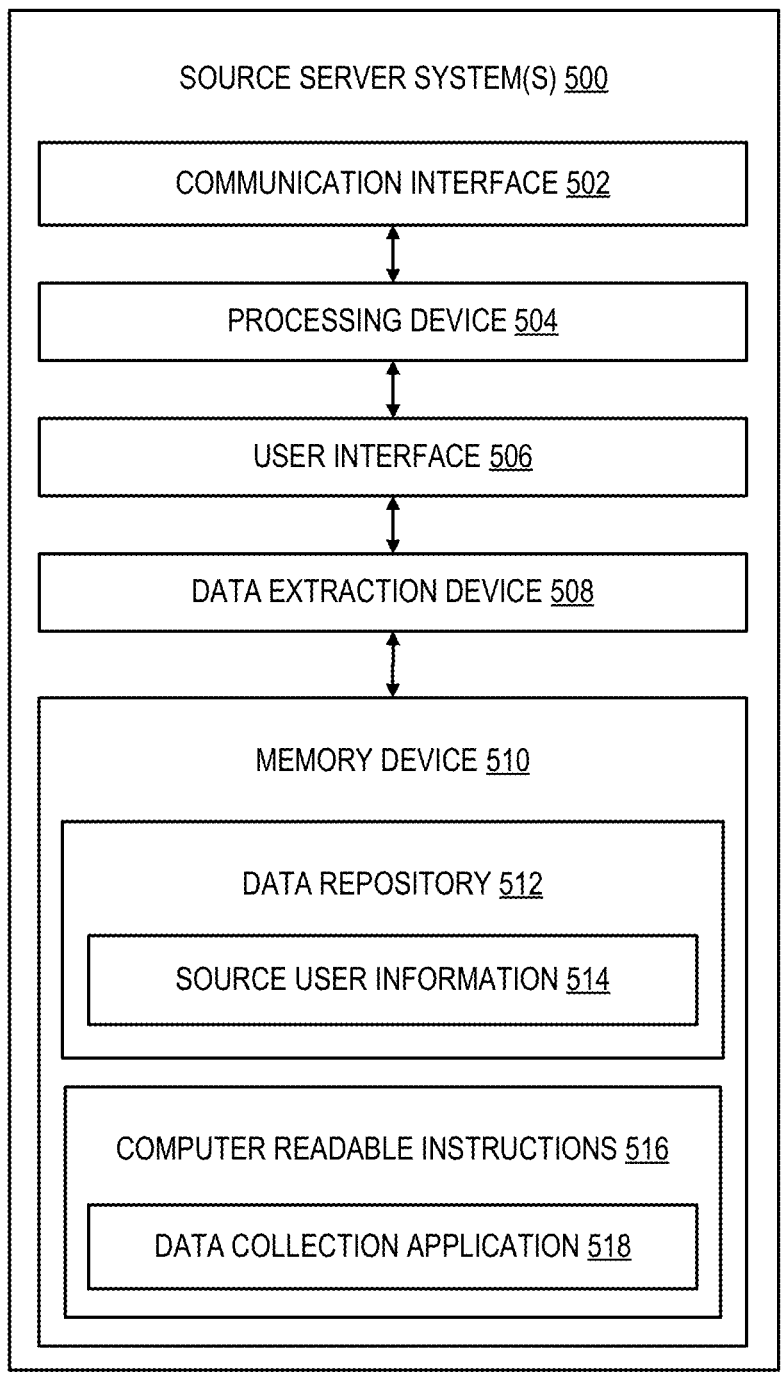
Figure 6:
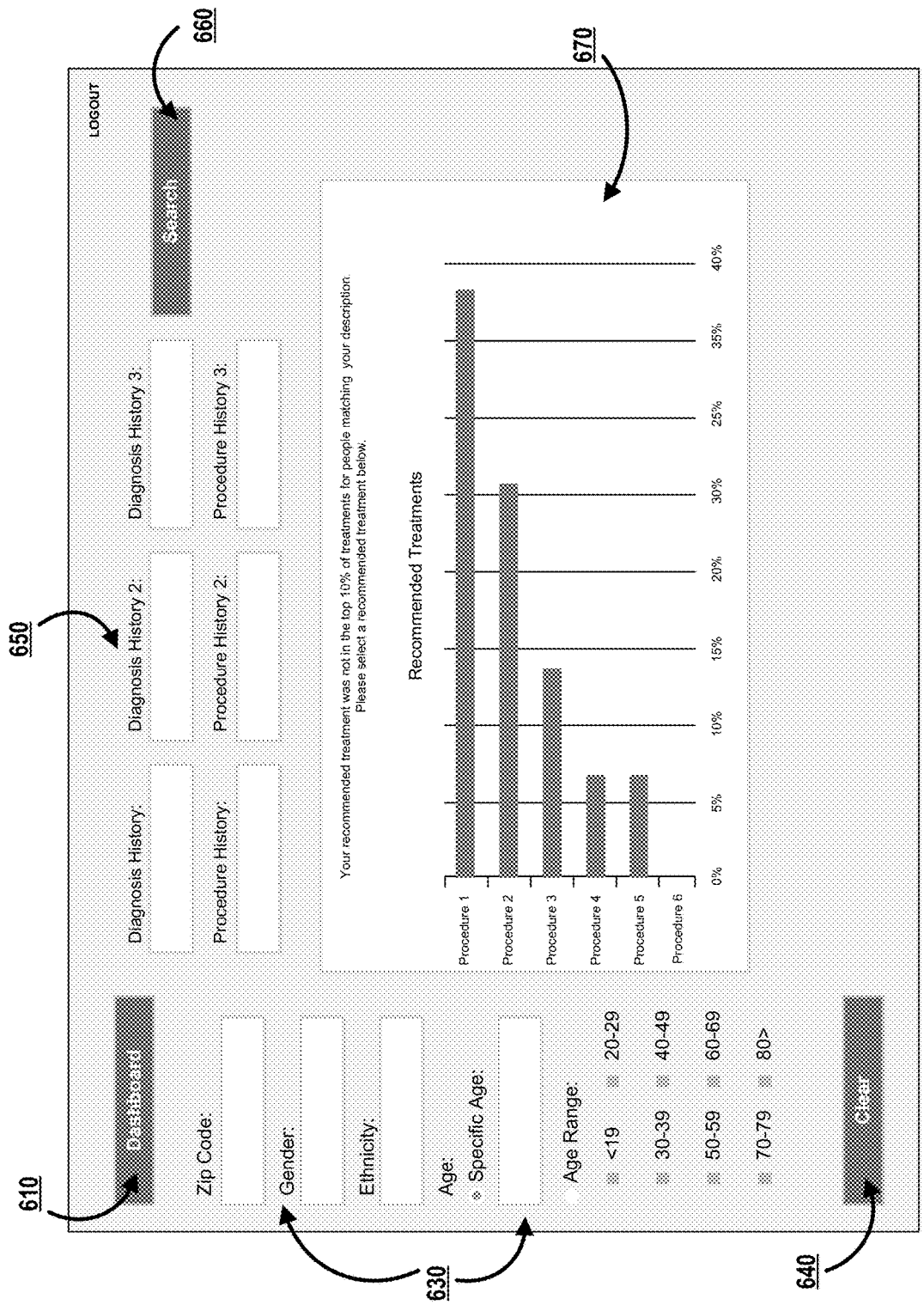
Figure 7:
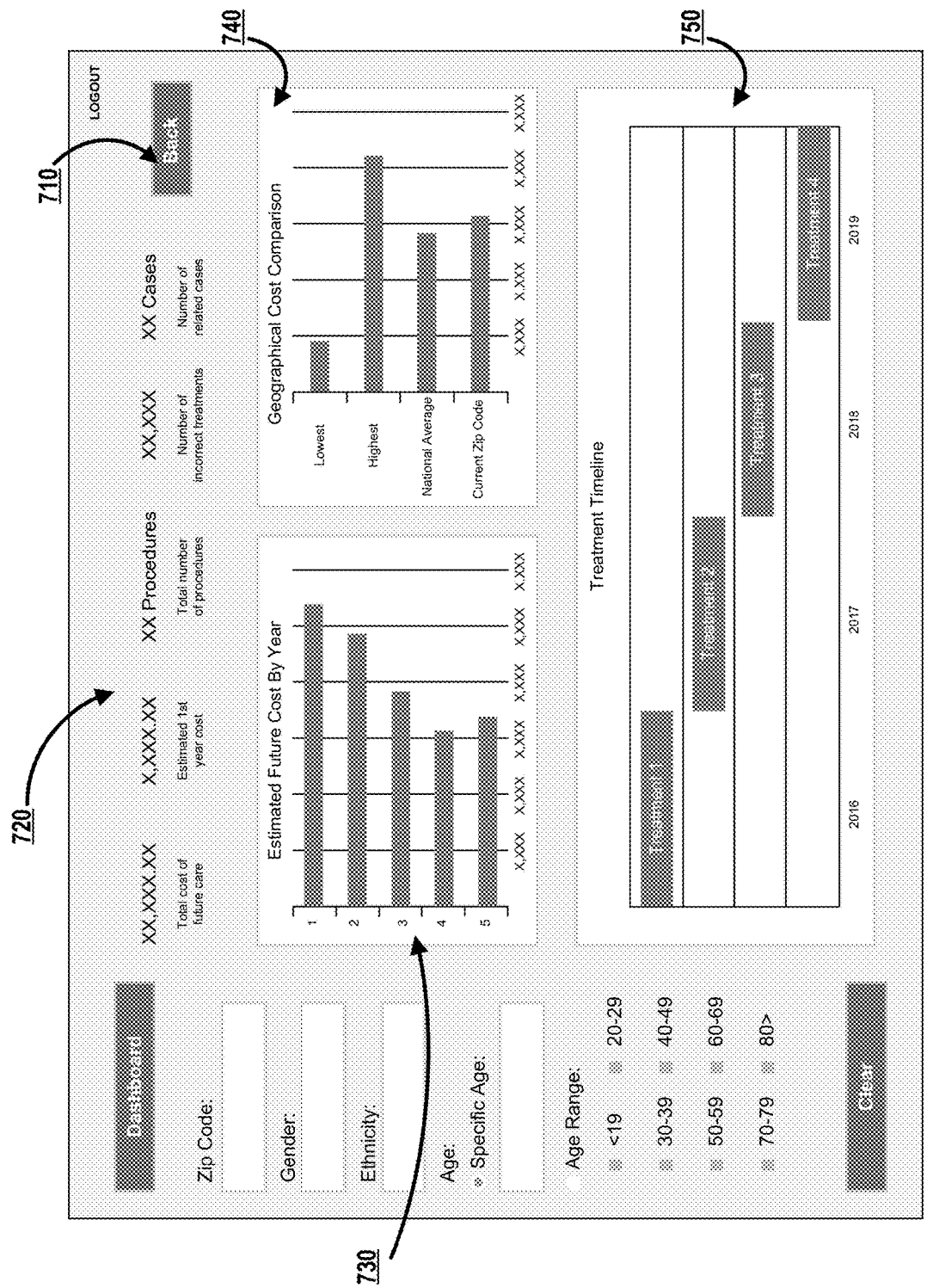
Figure 8A:
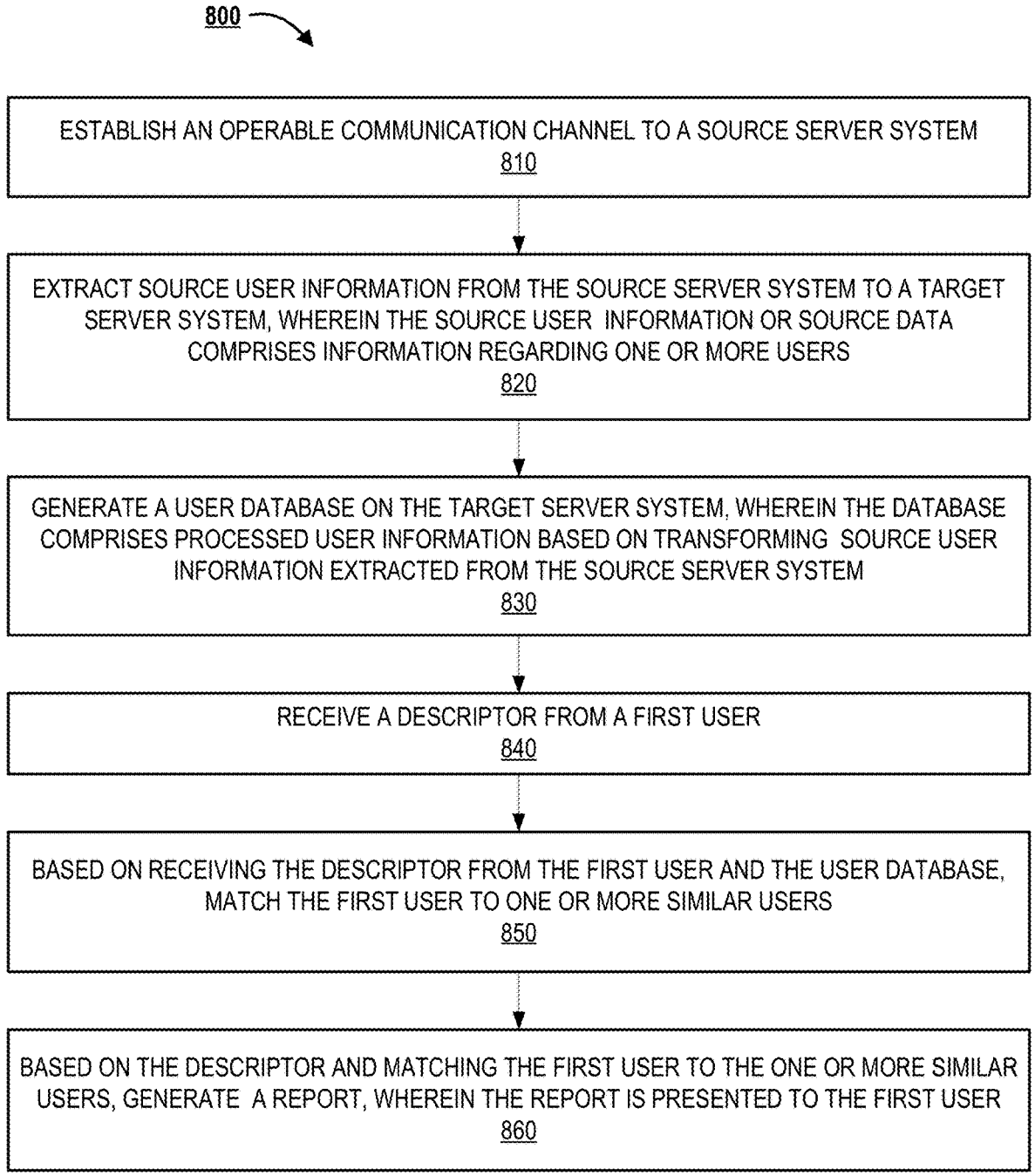
Figure 8B:
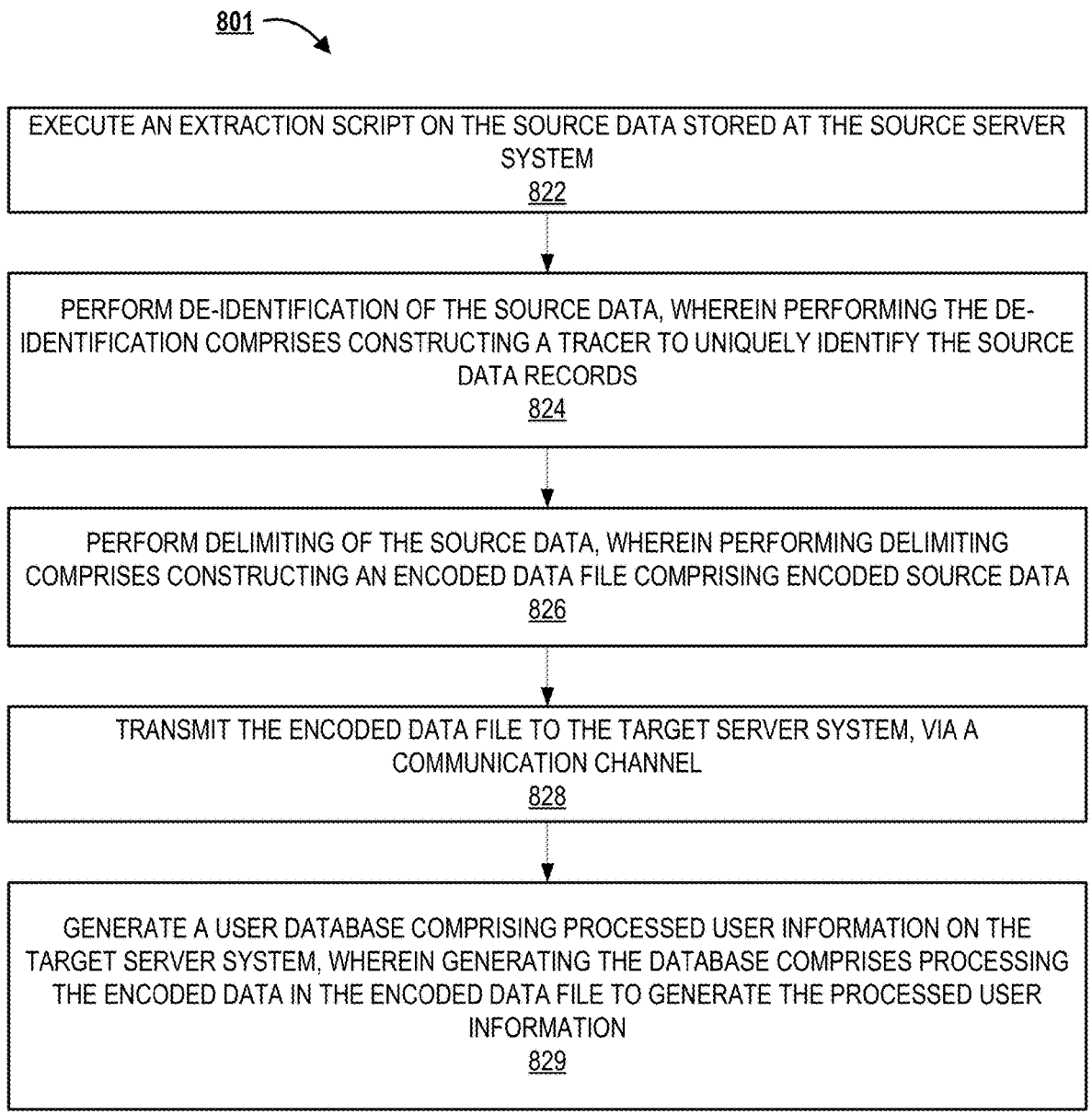
Figure 9:
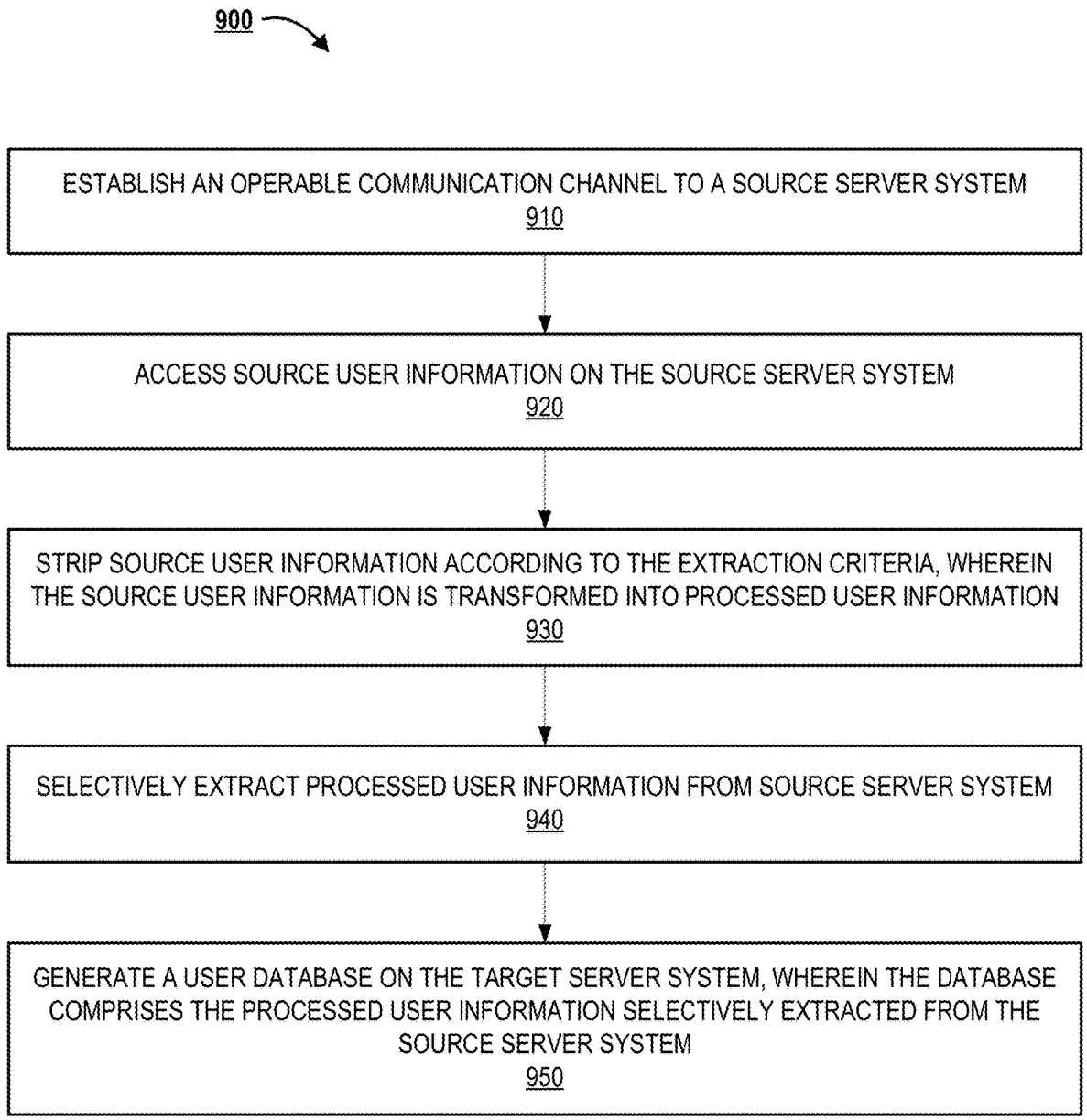
Figure 10:
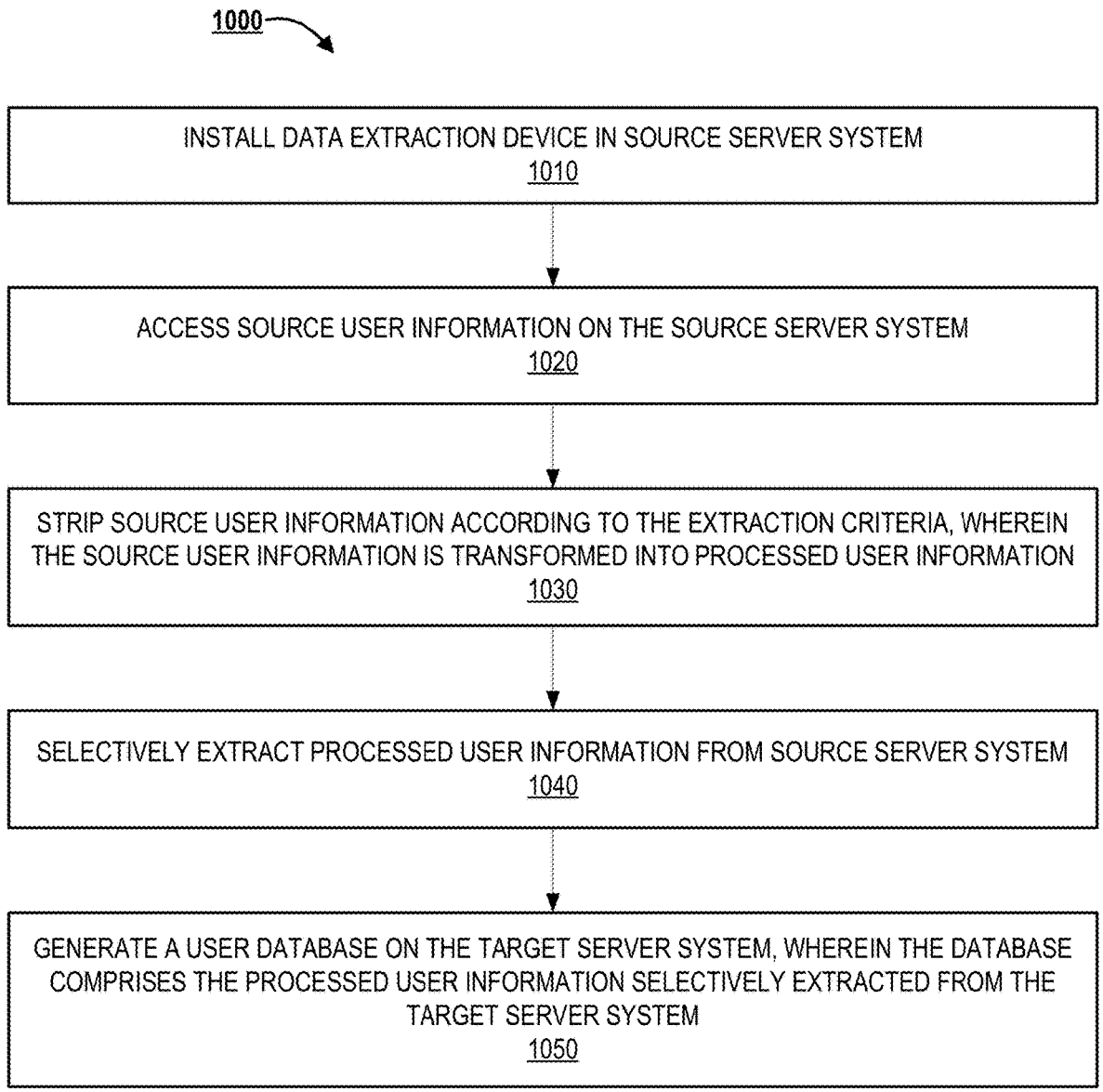
Figure 11:
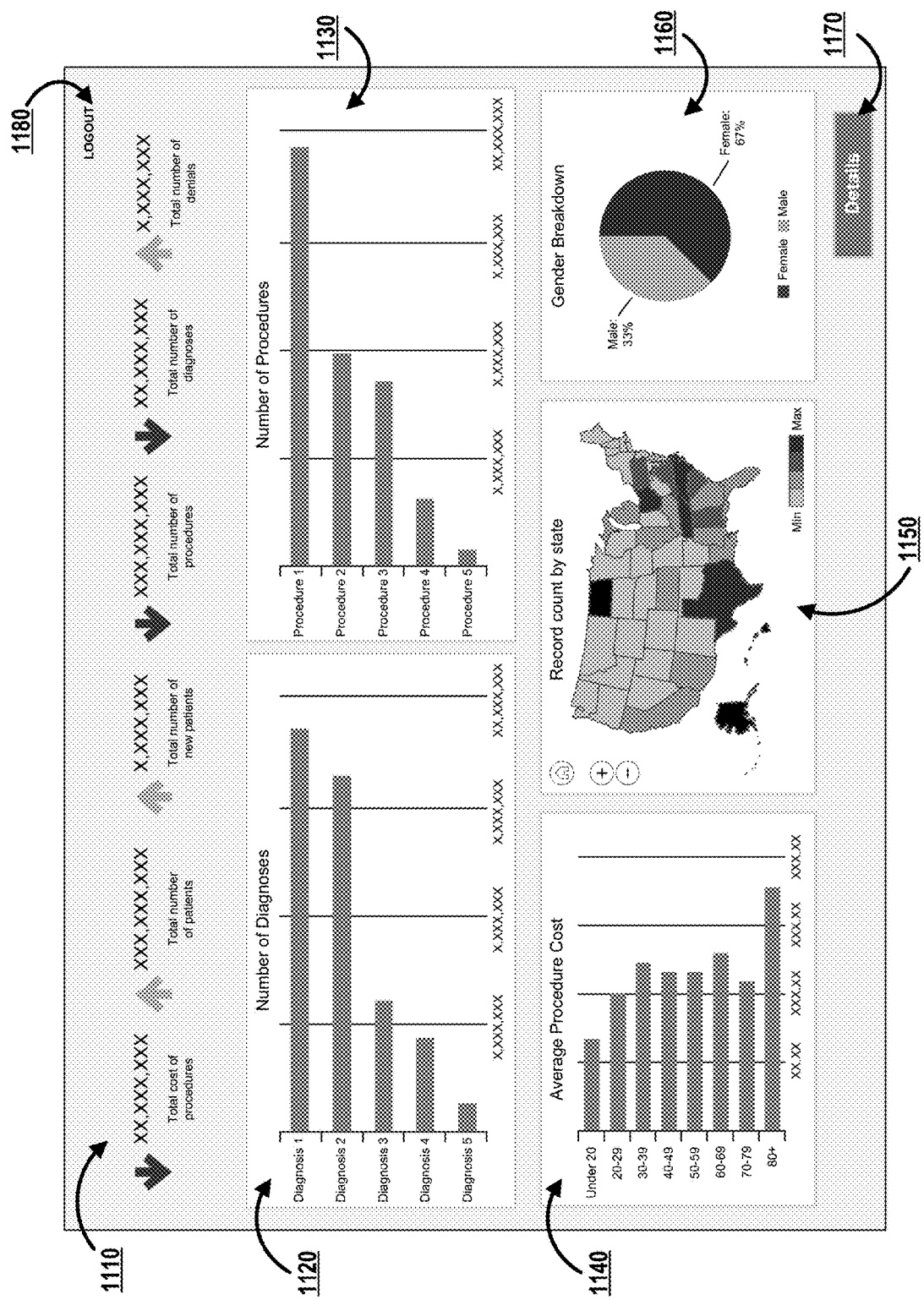

Having thus described embodiments of the invention in general terms, reference will now be made to the accompanying drawings, wherein:

FIG. 1 illustrates a selective data extraction and user correlation system environment 100, in accordance with some embodiments of the present invention;

FIG. 2 schematically depicts a user device 200, in accordance with some embodiments of the present invention;

FIG. 3 schematically illustrates a user correlation system 300, in accordance with some embodiments of the present invention;

FIG. 4 schematically illustrates a first source server system 400, in accordance with some embodiments of the present invention;

FIG. 5 schematically illustrates a second source server system 500, in accordance with some embodiments of the present invention;

FIG. 6 provides a graphical representation of a portion of a search function 600 for a predictive analytics application user interface, in accordance with some embodiments of the invention;

FIG. 7 proves a graphical representation of a portion of a treatment cost analysis function 700 for a predictive analytics application user interface, in accordance with some embodiments of the invention;

FIG. 8A provides a high level process flow 800 for user information extraction and user correlation, in accordance with some embodiments of the invention;

FIG. 8B provides a high level process flow 801 for user information extraction, in accordance with some embodiments of the invention;

FIG. 9 provides a high level process flow 900 for the selective extraction of user information from a source server system, in accordance with some embodiments of the invention;

FIG. 10 provides a high level process flow 1000 for the installation of a data extraction device and selective extraction of user information from a source server system, in accordance with some embodiments of the invention; and FIG. 11 provides a graphical representation of a portion of a landing page 1100 of a predictive analytics application user interface, in accordance with some embodiments of the invention.

DETAILED DESCRIPTION OF THE INVENTION

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to elements throughout. Where possible, any terms expressed in the singular form herein are meant to also include the plural form and vice versa, unless explicitly stated otherwise. Also, as used herein, the term "a" and/or "an" shall mean "one or more," even though the phrase "one or more" is also used herein. Furthermore, when it is said herein that something is "based on" something else, it may be based on one or more other things as well. In other words, unless expressly indicated otherwise, as used herein "based on" means "based at least in part on" or "based at least partially on."

A "user" as used herein may refer to any entity or individual associated with the data extraction and predictive analysis/analytics system. In some embodiments, the user may be an operator of a predictive analytics tool, data extraction application, and/or other applications and systems described herein. In some embodiments, a user may refer to a server administrator, database administrator, technician, analyst, software developer, or the like. In some embodiments, the user may be a patient seeking medical advice or diagnoses. In some embodiments, the user may be a physician, referred or referring physician, pharmacist, nurse, medical technician, medical personnel or an individual, system or entity associated with a patient. In yet other embodiments, a user may be a benefits manager, an insurance carrier, or an employee of an insurance carrier. A user may be a mobile device application user. In some embodiments, identities or identifying information of the user or an individual may include online handles, usernames, aliases, family names, maiden names, nicknames, predefined identifiers, alpha numeric codes, or the like. Furthermore, as used herein the term "user device" may refer to any device that employs a processor and memory and can perform computing functions, such as a personal computer or a mobile device, wherein a mobile device is any mobile communication device, such as a cellular telecommunications device (i.e., a cell phone or mobile phone), personal digital assistant (PDA), a mobile Internet accessing device, or other mobile device. Other types of mobile devices may include portable digital assistants (PDAs), pagers, wearable devices, mobile televisions, gaming devices, laptop computers, cameras, video recorders, audio/video player, radio, global positioning system (GPS) devices, or any combination of the aforementioned.

In accordance with embodiments of the invention, the term "entity" may be used to include any organization that collects and/or processes user information such as medical records, financial transactions, and user demographic information. These organizations may include, but are not limited to, hospitals, doctor's offices, medical facilities, businesses, financial institutions, insurance companies, and the like. As used herein, the term "source entity" is an entity that maintains a source server system or database, wherein data is collected and stored. As used herein, a "target entity" is an entity that extracts data from a source server system to a target server system. In some embodiments of the invention the terms "entity" and "user" may be used interchangeably.

As used herein, "data" is information collected, stored, extracted, processed and/or maintained on a system, such as a server or database. In some embodiments, data includes user information such as medical records, financial information, and demographic information. In some embodiments, the terms "data" and "user information" may be used interchangeably. The medical records are a collection of one or more users' medical information and history including, but not limited to, medical diagnoses, procedures, prescribed drugs, referrals, and the like. Financial information includes, but is not limited to, costs for medical visits, procedures, drugs, and the like that may be immediate or accrued over a period of time. Demographic information may include identifying information associated with a user such as age, ethnicity, gender, geographic location, income and the like. In some embodiments, the data may not be medical related and may be any data stored in a database.

In some embodiments, "data" or "user information" comprises source data. "Source data" typically refers to data or user information that is stored at, and/or that is extracted from a plurality of discrete source server systems. In some instances, source data refers to data stored in accordance with the format, content, structure, configuration, technical language and/or other data parameters of data storage of the source server system. In some embodiments, "data" or "user information" comprises "encoded data," which typically refers to transformed/processed source data. Here, in some instances, the format, content, structure, configuration, technical language, file type, and/or other data parameters/components of the source data may be transformed or modified during or after extraction of source data, to construct the encoded data. In some embodiments, transforming the source data to encoded data comprises delimiting, de-identifying, and/or otherwise fundamentally transforming, appending, and/or augmenting source data. In some embodiments, transforming the source data to encoded data facilitates data transmission across a communication channel. In some embodiments, "data" or "user information" comprises "processed user information," which typically refers to reconstructed/processed encoded data. For instance, the encoded data may be transmitted, via a communication channel, to a target server system, where the format, content, structure, configuration, technical language, file type, and/or other data parameters/components of the encoded data may be, reconstructed, transformed or otherwise modified to construct the processed user information.

Typically, "Authentication information" or "Authentication credentials" comprise any information that can be used to identify, authenticate and/or authorize a user. For example, a system may prompt a user to enter authentication information such as a username, a password, a personal identification number (PIN), a passcode, biometric information (e.g., voice authentication, a fingerprint, heart rate, predetermined physical gestures and/or a retina scan), an answer to a security question, and/or a unique intrinsic user activity, such as making a predefined motion with a user device. As a non-limiting example, this authentication information may be used to authenticate the identity of the user (e.g., determine that the authentication information is associated with an account) and, based on successful validation of the credentials, further determine that the user has authority to perform a certain user activity, (e.g., access an account or system).

In some embodiments, "monitoring" refers to determining, identifying, measuring, observing, comparing, analyzing, processing and/or checking a variable, a value, a quantity, and/or an amount for a predetermined process or purpose, over a period of time. The "monitoring" may occur periodically or intermittently over the period of time, or the monitoring may occur continuously over the period of time. In some embodiments, a system may actively monitor a database, wherein the system periodically transmits control signals to the database, the control signals being configured to retrieve predetermined source data from the database or being configured to cause the database system to transmit the predetermined source data, typically in real time, over a predetermined period of time. Next, the system, typically, identifies changes/modifications to the source data stored in the source database and/or additionally processes the predetermined source data retrieved from the database, for example, by utilizing the data to perform one or more additional steps, performing data delimiting, data de-identification, data stripping, data transformation and/or the like, to construct encoded data, typically stored in an encoded data file. As such, the system is configured to watch, observe, and/or check the database for changes, updates, and the like. In other embodiments, as described above, a system may passively monitor a database, wherein the database provides information to the system and the system then watches, observes, or checks the provided information. The "system" as described herein may refer to a user correlation system 300, which will be described in detail below.

Embodiments of the invention are directed to a system, method, or computer program product for selectively extracting source data and correlating users for predictive analysis. In some embodiments, the system (for example, the user correlation system 300 described below) accesses source data collected on one or more source server systems (and/or reconstructed, processed user information at the target system) and selectively extracts user information according to the desired criteria of an operator or user. The system generates a secure, user database, wherein the user database comprises the selectively extracted user information, such as medical, financial, and demographic information, from multiple source server systems creating a centralized database of user information stored in a single location. The system further provides a predictive analytics application to a user, via a user device. The predictive analytics application allows the user to input descriptors such as age, ethnicity, gender, diagnoses, medical procedures, and the like and receive a generated predictive analysis interface, such as a report presented on a user interface, the report comprising a comparative analysis of the user to one or more similar users determined by the system based on the inputted descriptors and the user information contained in the generated user database. Furthermore, the system displays predictive results for likely future diagnoses, procedures, and costs for the user based on the history of the similar users. Furthermore, the present invention is configured to securely utilize user information, by maintaining anonymity of the individuals associated with the extracted source data (for example, by de-identifying source data, i.e., by stripping out any personal and identifying information prior to or during extraction) and that of the user seeking to analyze his/her symptoms and diagnoses, while still enabling correlation of users and individuals and their medical data for predictive analysis.

In conventional systems, the extraction of data from a server or database typically involves, replicating large amounts of data, most of which may not even be pertinent, transferring/transmitting the data to a central system, analyzing each of the myriad data elements in the data, and processing each of the myriad data elements. These steps often need to be performed to, at least, determine pertinent data and data elements in conventional systems. As such, these steps consume a large amount of processing power for extraction, replication and analysis, require significant network/communication resource availability for transmission of the large volume of data, further require a large amount of memory for storage and processing of the data, and are extremely time consuming. However, data is typically required to be retrieved from multiple source server systems or databases, further multiplying or inflating the requirement of technical or computing resources, such as processing power, network requirements, memory requirements, and processing time at the centralized system. Further, a large portion of the processed data that is typically not relevant, and is discarded after aforementioned steps, causes an outsized wastage in the form of technical resources and time spent on the discarded data, squandering resources that may be better utilized for other applications.

As such, the extraction of large amounts of data from multiple source server systems such as patient record systems or billing software programs associated with a hospital or insurance carrier is normally a time and labor intensive process that can be taxing on the technical resources while requiring several hours or even days to complete. The present invention solves this technical problem by providing a unique technical solution involving distributed processing and leveraging resources of the source server systems for the processing at the disparate server systems, and transmitting only pertinent data, in an embedded form, to the target server system, such as the system 300. This typically involves de-identifying data stored on the source server systems, delimiting pertinent source data, selectively extracting only the data of interest to a target server system (such as the system 300) by transmitting the encoded data to the target system in an a processed data file of significantly smaller size, such as a text file comprising the processed delimited data. Moreover, the system strips the data of unwanted information such as anomalies, redundancies, and personal identifying information. In some embodiments, the system deploys a script or transmits a control signal/command to the source server system(s) to cause the source server system(s) to collect, delimit, and de-identify the targeted information before extraction. Furthermore, the system is configured to identify modifications to the data stored in source data system since the previous extraction. Consequently, the system only extracts the modified/added/new source data instead of the entirety of the source data including unchanged data.

In some embodiments, the system employs the decentralized computing resources of the source server systems (for example, during a predetermined downtime of the source server system, such as at night time, or based on determining that the source server system currently has idle, underutilized, or available technical resources) and associated computing devices within the source entity's network to collect and de-identify data in preparation for extraction. In these ways, the system improves the efficiency of the data extraction and user correlation process by reducing the amount of data needed to be pulled and reducing the time required for data extraction to a matter of minutes. Furthermore, the decentralized processing performed by the system efficiently utilizes and requires fewer processing resources, since the decentralized computing harnesses underutilized computing resources of the source server systems that typically would be otherwise wasted or unused during idle time/downtime. This further allows for the processing requirements at the target server system to be greatly reduced. As only pertinent data is transmitted to and processed at the target server system, the consumption of technical resources of the target server system on unwanted data that would eventually be discarded is minimized.

As an example, for a source server with source data in the size of around 469.68 GB, conventional processing systems require about 14.5 hours to replicate, extract and transmit the 469.68 GB of data. However, the present system provides a considerable improvement to existing methods. Specifically, for a source server with source data in the size of around 77 GB, the present system requires a mere 9 minutes to process the data, for example, by employing a script to determine pertinent source data, de-identifying the source data, delimiting the source data, creating an encoded data file with the source data, and/or transmitting the encoded data file to the target system. Furthermore, the extracted data from the 77 GB database is transmitted as a significantly smaller file of size 119.5 MB (such as a text file).

Embodiments of the present invention address the above needs and/or achieve other advantages by providing apparatuses (e.g., a system, computer program product and/or other devices) and methods for selectively extracting data and correlating users for predictive analysis/analytics.

Referring to FIG. 1, the figure illustrates a selective data extraction and user correlation system environment 100, in accordance with some embodiments of the invention. The environment 100 comprises a user device 200 associated with a user 104 and typically used with authorization of the user 104, a user correlation system 300, and one or more source server systems 400. As used herein, a "processing device," such as the processing devices 204, 304, 404, and 504 (described with respect to FIGS. 2-5, respectively), generally refers to a device or combination of devices having circuitry used for implementing the communication and/or logic functions of a particular system. For example, a processing device may include a digital signal processor device, a microprocessor device, and various analog-to-digital converters, digital-to-analog converters, and other support circuits and/or combinations of the foregoing. Control and signal processing functions of the system are allocated between these processing devices according to their respective capabilities. The processing device may further include functionality to operate one or more software programs based on computer-executable program code thereof, which may be stored in a memory. As the phrase is used herein, a processing device may be "configured to" perform a certain function in a variety of ways, including, for example, by having one or more general-purpose circuits perform the function by executing particular computer-executable program code embodied in computer-readable medium, and/or by having one or more application-specific circuits perform the function.

As used herein, a "user interface," such as the user interfaces 206, 306, 406, and 506 (described with respect to FIGS. 2-5, respectively), generally includes a plurality of interface devices and/or software that allow a customer to input commands and data to direct the processing device to execute instructions. For example, a user interface may include a graphical user interface (GUI) or an interface to input computer-executable instructions that direct the processing device to carry out specific functions. The user interface employs certain input and output devices to input data received from a user or output data to a user. These input and output devices may include a display, mouse, keyboard, button, touchpad, touch screen, microphone, speaker, LED, light, joystick, switch, buzzer, bell, and/or other customer input/output device for communicating with one or more customers.

As used herein, a "memory device," such as memory devices 208, 308, 408, and 510 (described with respect to FIGS. 2-5, respectively), generally refers to a device or combination of devices that store one or more forms of computer-readable media for storing data and/or computer-executable program code/instructions. Computer-readable media is defined in greater detail below. For example, in one embodiment, the memory device includes any computer memory that provides an actual or virtual space to temporarily or permanently store data and/or commands provided to the processing device when it carries out its functions described herein.

As used herein, a "communication interface," such as communication interfaces 202, 302, 402, and 502 (described with respect to FIGS. 2-5, respectively), generally includes a modem, server, transceiver, and/or other device for communicating with other devices on a network, and/or a user interface for communicating with one or more customers. A communication interface may have one or more communication devices configured to communicate with one or more other devices on a network, such as a user device, computer system, server system, cloud server system, and/or the like. The processing device is configured to use the network communication interface to transmit and/or receive data and/or commands to and/or from the other devices connected to the network.

The systems and devices communicate with one another over the network 102 via one or more communication channels 110 and perform one or more of the various steps and/or methods according to embodiments of the disclosure discussed herein. The network 102 and the one or more communication channels 110 may include a local area network (LAN), a wide area network (WAN), and/or a global area network (GAN). The network 102 may provide for wireline, wireless, or a combination of wireline and wireless communication between devices in the network. In one embodiment, the network 102 includes the Internet. In some embodiments, the network 102 includes wireless communication, such as near field communication. The one or more communication channels 110 allow the various systems of the environment to transmit and receive data, control signals, and commands to and from one another.

Referring now to FIG. 2, which schematically depicts a user device, in accordance with one embodiment of the invention, the user device 200 includes a communication interface 202 communicably coupled with a processing device 204, which is also communicably coupled with a memory device 208. In some embodiments, the communication interface 202 may also comprise a GPS transceiver capable of determining a geographic location associated with the user device 200. The processing device 204 is configured to control the communication interface 202 such that the user device 200 communicates across the network 102 with one or more other systems. The processing device 204 is also configured to access the memory device 208 in order to read the computer readable instructions 212, which in some embodiments includes a user application 214. The user application 214 allows for communication of the user device 200 with the other systems and devices within the environment 100 such as the user coordination system 300. The user application 214 allows the user 104 to receive information transmitted as well as input information requested by the other systems and communicate with entities and third parties within the system environment 100. In some embodiments, the computer readable instructions 212 include a predictive analytics application 216. The predictive analytics application 216, in some embodiments, generates and presents to the user a predictive analytics/analysis interface/report, for example, on the user interface 206, based on data from similar users. The memory device 208 also includes a data repository 210 or similar storage device for storing pieces of data that can be accessed by the processing device 204.

Referring now to FIG. 3, which schematically depicts a user correlation system, in accordance with one embodiment of the invention, the user correlation system 300 includes a communication interface 302 communicably coupled with a processing device 304, which is also communicably coupled with a memory device 308. The processing device 304 is configured to control the communication interface 302 such that the user correlation system 300 communicates across the network 102 with one or more other systems. The processing device 304 is also configured to access the memory device 308 in order to read the computer readable instructions 314, which in some embodiments includes a data extraction application 316. The data extraction application 316, in some embodiments, allows for the selective extraction of data and user information from one or more source server systems and/or user devices. The data extraction application 316 may also allow for communication with the other systems and devices within the environment 100 such as the user device 200 and the one or more source server systems 400. In some embodiments, the computer readable instructions 314 include a predictive analytics tool or a predictive analytics tool 318. The predictive analytics tool 318, in some embodiments, analyzes user input and extracted information in order to match a user with other similar users to generate a predictive analysis/analytics report. The memory device 308 also includes a data repository 310 or similar storage device for storing pieces of data that can be accessed by the processing device 304, such as extracted user information 312. In some embodiments, the extracted user information 312 is user information or other data extracted from one or more source server systems 400 and/or user devices 200. In some embodiments, the user correlation system 300 may be part of another system in the environment 100 such as the user device 200 or integrated into the one or more source server systems 400. In some embodiments, the data repository 310 having the extracted user information 312 is a virtual tape library (VTL) with a physical storage component such as hard disk storage, although tape drives may also be employed. Here, in some instances, the VTL comprises Serial Attached SCSI (SAS) or Serial AT Attachment (SATA) disk arrays as the storage component. These array enclosures enhance the scalability of the data repository 310 having the extracted user information 312, because the storage capacity may be increased by merely adding additional disk drives and enclosures.

Referring now to FIG. 4, which schematically depicts a source server system, in accordance with one embodiment of the invention, the source server system 400 includes a processing device 404 operatively coupled to a communication interface 402 and a memory device 408. The processing device 404 is configured to control the communication interface 402 such that the source server system 400 communicates across the network 102 with one or more other systems. The processing device 404 is also configured to access the memory device 408 in order to read the computer readable instructions 414, which in some embodiments include a data collection application 416. The data collection application 416 allows for the collection of data to be selectively extracted from the source server system 400 by a user correlation system 300, user device 200, and/or other system. In some embodiments, the data collection application 416 may also allow for communication with the other systems and devices within the environment 100 such as the user device 200 and the user correlation system 300. The memory device 408 also includes a data repository 410 or similar storage device for storing pieces of data that can be accessed by the processing device 404. In some embodiments, the data repository 410 includes source data or source user information 412 collected and stored in the one or more source server systems 400.

Referring now to FIG. 5, which schematically depicts an alternative embodiment of a source server system, in accordance with one embodiment of the invention, the source server system 500 may further include a data extraction device 508 in addition to the components discussed above. In some embodiments, the data extraction device is a module installed in the source server system 500 which collects and selectively extracts user information from the one or more source server systems to a user correlation system 300, user device 200, and/or other systems. The data extraction device 508 may be hardware and/or software installed in the source server system. In some embodiments, the data extraction device 508 is maintained by a source entity associated with the source server system 500. In other embodiments, the data extraction device 508 is maintained by a target entity or third party associated with the user correlation system 300 or other system configured to receive extracted user information from the source server system 500.

The user application 214, the predictive analytics application 216, the data extraction application 316, the predictive analytics tool 318, and the data collection application 416 are configured for instructing the processing devices on their respective systems to perform various steps of the methods discussed herein, and/or other steps and/or similar steps. In various embodiments, one or more of the various applications discussed are included in the computer readable instructions stored in a memory device of one or more systems or devices other than their respective systems and/or devices. For example, in some embodiments, the predictive analytics tool 318 may be stored and configured for being accessed by a processing device of the user device 200 connected to the network 102. In various embodiments, the user application 214, the predictive analytics application 216, the data extraction application 316, the predictive analytics tool 318, and the data collection application 416 are stored and executed by different systems/devices. In some embodiments, the discussed applications may be similar and may be configured to communicate with one another. In some embodiments, the various applications may be considered to be working together as a singular application despite being stored and executed on different systems.

In various embodiments, one of the systems discussed above, such as the user correlation system 300, is more than one system and the various components of the system are not collocated, and in various embodiments, there are multiple components performing the functions indicated herein as a single device. For example, in one embodiment, multiple processing devices perform the functions of the processing device 304 of the user correlation system 300 described herein.

In various embodiments, the user device 200, the user correlation system 300, the one or more source server systems 400, and/or other systems may perform all or part of one or more method or process steps discussed above and/or other method steps in association with the method steps discussed above. Furthermore, some or all the systems/devices discussed herein, in association with other systems or without association with other systems, in association with steps being performed manually or without steps being performed manually, may perform one or more of the steps of one or more of the method discussed herein, or other methods, processes or steps discussed herein or not discussed herein.

FIG. 11 illustrates a graphical representation of a portion of a landing page of a predictive analytics application user interface 1100, in accordance with some embodiments of the invention. As such, the system is configured to cause the user device(s) to present one or more interfaces associated with the medical diagnostic platform and the predictive analysis/analytics features. For example, in some embodiments, a landing page 1100 or a first user interface 1100 is presented to the user upon initially logging into the system or upon initial authentication/credential validation. The user interfaces (for example, the landing page 1100) may comprise a menu to enable the user to perform one or more functions or interact with the system. Furthermore, the menu of the landing page provides a logout option 1180 which allows the user to exit the application. Upon launching the application, the user may be prompted by the application to provide authentication information to log in, as discussed previously.

In some embodiments, the application provides a bar of vectors or quick numbers 1110 at the top of the screen, which may include total cost of procedures, total number of patients, total number of new patients, total number of procedures, total number of diagnoses, and total number of denials and the like. Each quick number may be associated with a corresponding arrow that indicates whether the number has increased or decreased since the last data pull from the source server systems (and/or last login by the user). In some instances, these vectors may be associated with the user, individuals with similar user profiles as that of the user, individuals associated with one or more predetermined entities or healthcare providers, individuals located within a predetermined geographic region, and/or the like.

A number of diagnoses graph 1120 displays the diagnoses associated with the user and how many times that diagnosis has occurred. In some instances, these diagnoses may be determined and displayed based on symptoms/procedures previously or currently input by the user, or procedures/symptoms of the user determined by the system. In some instances, these diagnoses may be predictive diagnoses determined based on past and/or current diagnoses of the user. In some instances, these diagnoses may be diagnoses of individuals with similar user profiles as that of the user. Individuals with similar user profiles as that of the user may include individuals with similar age (for example, aged within a predetermined years/months of the user's age), similarly situated individuals (for example, located/residing within a predetermined zip code, within a predetermined distance from the user, or located/residing in an area with similar parameters as the user), individuals with similar health/medical history as the user (for example, having at least one similar diagnosis/procedure), and/or the like. In some embodiments, the application may display the top ten diagnoses 1120 associated with a user (for example, predicted diagnoses of the user, diagnoses of similar individuals, previous diagnoses of the user and the like).

A number of procedures visual indicator, such as a graph 1130 displays the procedures associated to the user along with how many times that procedure has occurred. In some instances, these procedures may be determined and displayed based on symptoms/procedures previously or currently input by the user, the diagnoses of the user, diagnoses of individuals similar to the user, and/or procedures/symptoms of the user determined by the system. In some instances, these procedures may be predictive procedures determined based on past and/or current procedures and/or diagnoses of the user. In some instances, these procedures may be procedures undergone by, or recommended for, individuals with similar user profiles as that of the user, as described previously. In some embodiments, the application may display the top nine procedures associated with the user (for example, predicted procedures of the user, procedures of similar individuals, previous procedures of the user and the like).

In some embodiments, an average procedure cost graph 1140 displays the cost of the average procedure for a number of age groups. In some embodiments, a record count by state chart 1150 displays how many records exist in the system for each state (for example, the total number of available records or number of records of individuals similar to the user). In some embodiments, the user may view the record count by scrolling over the desired state. In some embodiments, the record count may be for areas other than states such as cities, counties, regions, countries, or other geographical areas. In other embodiments, the record count may be provided based on another statistic other than geographic location. For example, the record count may be provided based on ethnicity, age, gender, or the like. In some embodiments, the record count may be based on a count of records associated with one or more diagnoses or procedures. In some embodiments, a gender breakdown 1160 chart, displays a percentage breakdown of the record data based on gender associated with the data. A details button 1170, in some embodiments allows the user to navigate to a detailed diagnostic page allowing for user input.

FIG. 6 illustrates a graphical representation of a portion of a search function of a predictive analytics application user interface 600, in accordance with some embodiments of the invention. In some embodiments, predictive analytics application 216 is the user interface 214 and allows for detailed medical diagnostics based on user input. The application allows the user to input user information, such as commands (for example, desired timeline for prediction (immediate, after a predetermined period of time, and the like), desired output (treatments, procedures, diagnoses, and the like)) or data (for example, past or current symptoms, procedures, diagnoses/recommendations by physicians, medication, and the like), into a user device, and allows the device to output information to the user. As illustrated in FIG. 6, in some embodiments, the application presents the user with means for navigating the interface by providing dashboard button 610 to return to a the landing page of the application. In some embodiments the dashboard button may provide a drop-down menu which provides the user with additional interactive selections for navigation within the application. The application provides data input elements, such as fillable fields or text boxes 630 for the user to enter one or more descriptors or user profile information, such as, but not limited to, zip code, gender, ethnicity, and age. Additionally, the application provides another data element, such as a button feature for a clear option 640 to reset the fillable fields. In some embodiments, the application allows for the user to enter a specific age or an age range. The application further provides diagnosis and procedure fields 650 for the user to input the corresponding information, such as past and/or current diagnoses and their respective procedures. In some embodiments, the application allows for the user to input one or more symptoms in order to receive a diagnosis or receive a validation of the current diagnosis. As shown in FIG. 6, the user is able to input several diagnoses, procedures and symptoms (not shown). In some embodiments, the application provides a search button 660 to initiate the generation of a predictive analysis/analytics report based on the user's input into the various fields of the application.

In some embodiments, upon searching, the application may provide the user with a list of recommended diagnoses, procedures, and/or treatments 670. In some embodiments, the application may further communicate with the user or display within the application whether the user's inputted diagnosis and/or procedure is within a threshold of most probable diagnoses and/or procedures based on data associated with other users similar to the user. For example, the non-limiting embodiment illustrated in FIG. 6 communicates to the user that a treatment (or procedure) input by the user is not in the top 10% of treatments (or procedures) for people matching the user's description/profile. In some embodiments, the user may select or interact with one or more of the displayed recommended treatments to navigate to a detailed cost analysis associated with the selection.

FIG. 7 illustrates a graphical representation of a portion of a treatment cost analysis for a predictive analytics application user interface presenting comparative results 700, in accordance with some embodiments of the invention. The application provides a predictive analysis/analytics report displaying cost information of predicted costs of future care based on the information of similar users or individuals with similar user profiles. In some embodiments, the application provides a collection of vectors or statistical information 720 to present to the user such as the predicted costs of future care, a total number of procedures, a number of incorrect treatments, and a number of related cases. The application provides a back button 710 to allow the user to return to the previous search page as depicted in FIG. 6. In some embodiments, the application generates graphs tracking costs of treatments and procedures based on time and geographical location as shown by 730 and 740 respectively. The application also provides a timeline of predicted treatments 750 based on the information associated with other similar users. In some embodiments, the treatment timeline displays each possible procedure that may be recommended for the user over a period of time. For example, the application may provide the procedures that may be necessary for a user to receive over the course of the next five years. Although described with respect to interfaces 1100, 600 and 700, it is understood that one or more features/elements associated with these interfaces may be combined, moved into other interfaces or augmented with additional features.

FIG. 8A provides a high level process flow for user information extraction and user correlation 800, in accordance with some embodiments of the invention. As illustrated in block 810, the process 800 is initiated by the system first establishing operative communication channels with each of the one or more source server systems. The operative communication channels between the user correlation system and the one or more source server systems may be established over a wired or wireless connection, or a suitable combination, as described previously. The operative communication channel may comprise one or more of a wireless communication channel (for example, a channel utilizing radio waves), a mobile internet connection, a hotspot network channel (for example, a channel having network/internet access over a wireless local area network via a router, a Wi-Fi communication channel for wireless data exchange through radio waves, and the like), a dial-up channel (for example, a communication channel operated through a telecommunication or a phone line), a broadband communication channel (for example, a digital subscriber line (DSL) channel), a wireline channel (for example, a channel utilizing electrical, electronic, light/optical frequency signals, and the like), a cable channel (for example, a channel using a cable modem), a satellite channel, an integrated services digital network (ISDN) channel, and/or the like, or a suitable combination of the above.

In some embodiments of the invention, the system establishes operative communication channels with the one or more source server systems over a network, such as the internet. In other embodiments, the communication channel is established over a secure, private connection between the system and the one or more source server systems in order to enhance security of extracted data. In some embodiments, the source server system may be a database or server system associated with a hospital, doctor's office, medical facility, an insurance provider, a pharmacy and/or the like, wherein the data stored in the database or server system includes user information such as medical records associated with the one or more users, wherein the one or more users may be patients who visited the hospital, doctor's office, or medical facility. In some embodiments, the source server system may be maintained by a source entity. In other embodiments, the source server system may be hosted by the target entity or a third party entity, wherein the target entity or third party entity maintains the source server system.

In some embodiments, establishing the operative communication channel between the user correlation system 300 and the source server system 400 (or the source server system 500) comprises transmitting to and installing the data extraction device 508 on the source server system, from the system 300. The data extraction device 508 is typically stored on the memory device (408, 508) of the source server system, and is typically accessible and executable by the processing device (404, 504) of the source server system. The data extraction device 508 typically comprises an encoding application, such as a normalization application, having computer readable instructions (or a computer executable script) that when executed by a processing device (such as the processing devices 404, 504 of the source server system) cause the processing device and/or other devices/components of the source server system to perform one or more steps described herein.

In some embodiments, the system 300 is configured to transmit control instructions (for example, via the communication interface (402, 502)) that cause the processing device (404, 504) to store, install, and/or execute the computer readable code of the data extraction device 508. During execution, the data extraction device 508 typically utilizes the processing resources and memory resources of the source server system. In some embodiments, the computer readable instructions of the data extraction device 508 are dynamic and may be modified by the system 300, in real time or in near real time. The data extraction device 508 is configured for extracting source data or source user information from the source server system, encoding the extracted source data, creating an encoded data file comprising the encoded data and transmitting it to the system 300 (or target server system), normalizing, delimiting, de-identifying and processing the data at the source server system itself prior to transmitting the data to the system 300, determining downtime of the source server system, determining resource underutilization and resource availability at the source server system for data processing, determining appropriate communication channels and consequently routing the extracted and processed source data, and the like. Typically, in the instances where the entities associated with the system 300 and the source server systems are distinct, the entities may enter into security, operation, and other agreements, to facilitate installation of the data extraction device 508 on, and extraction of data from the source server systems.

As illustrated in block 820 of FIG. 8A, the system extracts data in the form of source data or source user information, typically stored in memory devices/databases, from the one or more source server systems to a target server system (system 300). In some embodiments, the source data or source user information comprises user information from one or more users such as medical records, financial information, and demographic information. As previously discussed, medical records may be a collection of one or more users' medical information and history including, but not limited to, medical diagnoses, procedures, prescribed drugs, referrals, physician notes, tests/procedure results, and the like. Medical records may further include International Classification of Diseases (ICD) codes for identifying diagnoses and procedures. Financial information may include, but is not limited to, costs for medical visits, procedures, drugs, and the like that may be immediate or accrued over a period of time. Demographic information may include identifying information associated with a user such as age, ethnicity, gender, geographic location, income and the like. In other embodiments, the data may not be medical related and may be any data stored in a database.

In some embodiments, the system 300, for example, via the data extraction device 508, is configured to determine whether the source server system has underutilized or available resources prior to commencing the data extraction activities. In some embodiments, the system 300 and/or the data extraction device 508 may determine that the source server system currently has available or underutilized or idle technical or computing resources (such as processing power, memory availability, communication portal availability, and the like), in real-time or near real-time. In some embodiments, the system 300 and/or the data extraction device 508 may determine that the source server system typically has underutilized or available technical resources during a predetermined downtime (for example, during nighttime, or 11 PM to 4 AM), and initiate the data extraction based on at least determining that the current time is within the predetermined downtime. As such, the system 300 and/or the data extraction device 508 are configured to initiate the data extraction (for example, by deploying a script in real time or near real time), based on (i) determining that source server system currently has available or underutilized technical resources and (ii) determining that the technical resources will be likely available for a first predetermined period of time determined to be required for completion of the data extraction process (for example, the search, retrieval, normalization, and transmission of the source data), or required for completion of at least a portion of the data extraction processes. Accordingly, the system efficiently utilizes and requires fewer processing resources. The decentralized computing harnesses underutilized computing resources of the source server systems that typically would be otherwise wasted or unused during idle time/downtime. By instead employing the latent resources of the source server systems, the processing requirements at the target server system are greatly reduced.

In some embodiments, the source data or source user information may be unprocessed and stored within the source server system as it was initially collected such as within software or an application used to input patient information or a billing software program. In other embodiments, the source data or source user information may be collected and structured by the system such as within a table. Typically, the system 300 extracts source data from a plurality of discrete source server systems, with each source server system having disparate and different forms of data storage (for example, data stored in varying formats, syntaxes, data structures, and the like), and different operating methods (for example, different technical languages or operating syntax). For example, a first source server system may store data in a descriptive/written format with sentences or phrases (which may be required to be parsed by the system 300, and particularly the data extraction device 508), a second source server system may store data in an unordered or random way (for example, using heap files), a third source server system may store data using ordered rows and columns, while a fourth source server system may store data using a hash function. Because these source server systems may operate on different platforms, operating systems, technical languages and character sets, the various records received at the data processing system may be different from one another in their structure, format, syntax, technical language, character sets and other aspects, such as XML (Extensible Markup Language) format, EBCDIC (Extended Binary Coded Decimal Interchange Code) format, and the like.

The data or data records of the source server systems is typically encoded, i.e., transformed, formatted, processed, or otherwise fundamentally altered during the data transformation operations performed by the data extraction device 508. This data transformation is typically performed by the system 300, via the data extraction device 508 at the respective source server system using the resources of the source server system, by delimiting the source data, de-identifying the source data, and performing other operations, for example, to correct redundancies, to eliminate defects, to transform the data to a uniform format and/or to reduce or compress the file size of the resulting encoded data file. The encoding of the source data to transform the source data into the encoded data file is described in detail with respect to FIG. 8B, later on in this disclosure.

In some embodiments, the system, for example via the data extraction device 508, defines a dataset within a table that is delimited allowing the system to selectively identify and extract specific data points or datasets from the table structure without pulling unnecessary or additional information that is not pertinent. In some embodiments, the system transmits a command to instruct the source server system to collect and structure the user information. In some embodiments, the system may utilize the processing resources of the one or more source system servers and associated computing devices within the source entity system to process and export the collected data. Furthermore, in some embodiments, formatting the event record comprises transforming the technical language, syntax, attribute formatting, character set (for example, Binary Coded Decimal (BCD), ASCII, Unicode, Extended Binary Coded Decimal Interchange Code (EBCDIC), and the like), character encoding system of the data and the like into a predetermined standard format and/or into a predetermined format required for processing by the subsequent technology platform application.

As discussed previously, in some embodiments, the system deploys an extraction script or computer readable instructions or commands to the source server system, via the data extraction device 508, to selectively extract source data or source user information or other data, as described in detail with respect to FIG. 8B. The deployed script or command may selectively extract specific data points or datasets from the source server system. In this way, the system does not need to extract the entirety of the data stored on the source server system, but instead, may quickly and efficiently extract only the data of interest. In some embodiments, the script is deployed using the processing systems/devices/resources of the associated source server system. Furthermore, in some embodiments, the system, via the script, is configured to normalize the extracted source data or source user information. In some embodiments, the script is constructed in T-SQL (Transact-SQL) technical language, for example, to extract data from or interact with the source server system, such as a relational database. In some embodiments, the script is constructed in technical languages such as VB.net, C#, Java script, and the like. In some embodiments, the script is constructed in PL/SQL (Procedural Language/Structured Query Language) technical language. In other embodiments, the script may be constructed in technical languages such as ECL, K, PL/pgSQL, PL/Perl, SQL/PSM, and the like.

In some embodiments, the system may selectively extract and encode user information or source data from the source server system in response to a user requesting a predictive analysis/analytics report via an application. In other embodiments, the system may extract and encode source data from the source server system at regular intervals such as daily, weekly, or the like. In some embodiments a user may set extraction criteria or rules to designate data of interest to be extracted. For example, a user may wish to only extract information associated with one or more users' gender, age, diagnoses, and received medical procedures. In these ways, the system improves the efficiency of the data extraction and user correlation process by reducing to amount of data needed to be pulled and reducing the time required for data extraction to a matter of minutes (which would have previously required a day or two).

In typical implementation scenarios, the unique encoding, delimiting, de-identifying and normalization features of the invention drastically reduces the file size of the transmitted source data in comparison with conventional methods (for example, reduction from a conventional file size in the range of hundreds of gigabytes to a file size in the range of a few tens of gigabytes, such as reduction from 500-600 gigabytes to 50-60 gigabytes), and further reduces the transfer times (for example, the present invention enables records in the range of 150 Million to be transferred in 10 minutes instead of a few days required for conventional processing). As another example, for a source server with the source data in the size of around 469.68 GB, the conventional processing systems require about 14.5 hours to replicate, extract and transmit the 469.68 GB of data. However, the present system provides a considerable improvement to existing methods. Specifically, for a source server with the source data in the size of around 77 GB, the present system requires a mere 9 minutes to process the data, for example, by employing a script to determine pertinent source data, de-identifying the source data, delimiting the source data, creating an encoded data file with the source data, and/or transmitting the encoded data file to the target system. Furthermore, the extracted data from the 77 GB database is transmitted as a significantly smaller encoded data file of size 119.5 MB (such as a text file).

As discussed previously, the operative communication channels established between the system 300 and the source server system may comprise one or more of a wireless communication channel, a hotspot network channel, a Wi-Fi communication channel, a dial-up channel, a broadband communication channel (for example, a DSL channel), a wireline channel, a cable channel (for example, a channel using a cable modem), a satellite channel, an integrated services digital network (ISDN) channel, and/or the like, or a suitable combination of the above. Each of these channels is typically associated with a specific bandwidth range, a throughput range, a transfer rate range, and other properties or capabilities. For example, a dialup/modem channel may have bandwidths (net bit rates) in the range of 56 kbit/s, an asymmetric digital subscriber line (ADSL) channel (such as a G.992.2 channel, a ADSL2+ channel and the like) may have bandwidths in the range of 1.5-24 Mbit/s, an Ethernet channel may have bandwidths in the range of 10-100 Mbit/s (or a 100 Gigabit Ethernet channel may have bandwidths in the rage of 100 gigabits), an IEEE 802.11b wireless channel may have bandwidths in the range of 11 Mbit/s, an IEEE 802.11g wireless channel may have bandwidths in the range of 54 Mbit/s, a universal serial bus (USB) channel may have bandwidths in the range of 5 Gbit/s, and the like.

For transfer of extracted source data, using conventional methods, the file transfer often requires a specific type communication channel that is capable of transferring the large amounts of data (for example, a specific channel having a predetermined bandwidth and throughput capabilities, and estimated file transfer rate for the conventional file size). The initiation of file transfer may be delayed if the required communication channel is unavailable or occupied, and the file transfer through the communication channel itself is often slow due to the large file size. However, the unique data encoding, delimiting, de-identifying and normalization features of the invention and the resulting smaller size of the encoded data file enables the present invention to transfer files through a variety of communication channels and with increased speed. For example, based on determining that a first wireless communication channel with a first bandwidth and file transfer rate is currently busy, the system may route the encoded data file comprising the encoded source data, through another second communication channel with a second bandwidth and file transfer rate for the source data, even though the performance parameters of the second channel may be less than/inferior to the parameters of the first channel, which would typically not support file transfer of conventional data extraction. In this regard, the system is configured to switch channels and/or establish new communication channels to reduce wait times, while still enabling the file transfer faster than conventional methods.

As illustrated in block 830 of FIG. 8A, the system generates a user database on the target server system, wherein the database comprises the source data or source user information extracted from the one or more source server system. Typically, the system constructs the user database on the target server system with processed user information, based on receiving, at the target server system, the encoded data file, processing the data file, and reconstructing the processed user information based on parsing the encoded data in the encoded data file. In some embodiments, the user database is a centralized repository of data or processed user information extracted from the one or more source server systems and collected and stored in the target server system to be accessed and used by the system for predictive analysis/analytics. In some embodiments, the user database is a collection of extracted medical, financial, and demographic information associated with one or more users. By collecting large amounts of data from multiple sources, the system is able to increase the accuracy of its predictive analysis, diagnoses, and recommendations. In some embodiments, input from a user within the predictive analytics application requesting a medical diagnostic may be extracted and stored in the user database, wherein the size of the user database is built upon and continually grows with continued user interaction. Extracted data may be indexed and further structured within the generated user database by the system to further optimize data retrieval. For example, the extracted data may be indexed, grouped, or otherwise categorized based on one or more common aspects of the extracted information such as common diagnoses, procedures, or treatments. In some embodiments, the data may be indexed based on geographic and/or demographic information. For example, data may be indexed, grouped, or categorized based on being associated with a common zip code. In another example, the data may be indexed based on gender, such as all female records being grouped together. Indexing and structuring the potentially large amounts of data in this way allows for the system to quickly retrieve stored data and provide results to the user for predictive analysis/analytics. In some embodiments, the processed user information in the user database may be structured/indexed in a B-tree structure or another data organizational structure.

The process continues in block 840 of FIG. 8A, wherein the system receives at least one descriptor from the user. In some embodiments, the system receives a descriptor from a user via a user application and/or predictive analytics application stored on a user device. A descriptor may be any identifying information that can be used to determine similar users from the user information stored within the user database and allow for predictive analysis/analytics and medical diagnostics. For example, a descriptor may be a diagnosis, symptom, procedure, treatment, ICD code, age range, gender, ethnicity, geographic location or the like input by the user and received by the system.

As illustrated in block 850 of FIG. 8A, based on receiving the descriptor from the user and the generated user database, the system matches the user to one or more similar users. Similar users/individuals are those users associated with the extracted user information who have been determined to be substantially similar to the first user based on a comparison of the one or more descriptors input by the user and the extracted user information stored in the user database. For example, based on the user inputting an age and an ICD code, the system may match the user with similar users of the same age who are associated with the same ICD code. In some embodiments, the system may automatically retrieve and provide an ICD code based on the user's inputted description of a diagnosis, procedure, or treatment. In this way, the user is not required to remember and input the specific ICD code in order to be presented with accurate results. In some embodiments, the system may require the user to at least provide a gender and age range in order to match the user with similar users and provide an analysis.

Typically, matching the user to one or more similar users based on the descriptors typically involves constructing multiple filters and suitably stacking the filters to determine the most relevant data. Here, the system sequentially applies the filters over decreasing/telescoping sizes of subsets, instead of applying all filters to the entire processed user information dataset. For example, for the descriptors, zip code 1, diagnosis 3, and age group 4, the system may construct and employ a first filter for the zip code 1, to determine a first subset of processed user information associated with the zip code 1. Next, the system may apply a second filter for the diagnosis 3, on the previously obtained first subset to determine a second subset of the first subset associated with both the zip code 1 and the diagnosis 3. In this way, the system may sequentially apply the filters, until the subset associated with the one or more similar users is obtained. In this way, the received data may be targeted and tailored to the user based on the descriptors allowing the system to quickly and efficiently match the user to the similar users based on a smaller, more focused subset of data while using less processing and memory resources.

As illustrated in block 860 of FIG. 8A, based on the descriptor and matching the user to the one or more similar users, the system generates a predictive analysis/analytics report, wherein the report is presented to the user. In some embodiments, the predictive analysis/analytics report provides one or more outcomes based on the received descriptors and the similar users. In some embodiments, the one or more outcomes may be recommended or predicted diagnoses, treatments, procedures, or the like. In some embodiments, the system includes an analytics algorithm that receives the information input by the user and estimates or extrapolates the most likely outcomes and probabilities associated with each outcome based on the user information associated with the determined similar users. In some embodiments, the system removes outliers from the data using standard deviations. For example, the system may only include data points from the determined similar users within two standard deviations of the statistic of interest and consider other data points as outliers.

In some embodiments, the predictive analysis/analytics report provides the user with a diagnosis based on symptoms input by the user. In some embodiments, the system displays the diagnoses of one or more similar users based on the user information stored in the user database. In other embodiments, the system may receive the symptoms of the user as well as a diagnosis previously received by the user and display a comparison of the user's previous diagnosis with the diagnoses of the one or more similar users. In this way, the system may determine the accuracy of a user's previously received diagnosis and one or more probable outcomes based on the user information associated with the similar users collected and stored in the user database allowing the user to receive a second opinion. In some embodiments, the report may display and rank or otherwise order the diagnoses of the similar users based on which diagnosis was more common.

For example, a user may have recently visited a doctor and received a diagnosis for a cold. The user then inputs his symptoms and received diagnosis into the predictive analytics application along with other descriptors such as age, ethnicity, gender, and the like. Based on the input symptoms, diagnosis, and other descriptors, the system matches the user to one or more similar users and provides a report. In this example, the report shows that based on the information associated with similar users, the most probable diagnosis is actually a sinus infection and that the original diagnosis of a cold is in the minority of diagnoses associated with the similar users.

In another example, a benefits manager of a company may wish to evaluate the accuracy of the diagnoses of a doctor commonly recommended by the company to its employees. Based off of the most common diagnoses provided in a report, the benefits manager might determine that the recommended doctor's diagnoses are consistently in the minority of diagnoses and that the doctor commonly misdiagnoses patients leading the company to resend its recommendation of the doctor.

In some embodiments of the invention, the predictive analysis/analytic report may further provide commonly recommended procedures and prescription and non-prescription drugs in response to receiving and/or generating a diagnosis based on the user information associated with the determined similar users. The system may display and rank the procedures or drug associated with the similar users based on which procedures or drug prescriptions were more common. For example, in response to diagnosing the user with a sinus infection, the system may determine based on the determined similar users, that the most probable recommended procedure would be a regimen of antibiotics. The system may further report the antibiotics most commonly prescribed to the similar users. In this way, the system may help the user in evaluating a recommended procedure, treatment, drug, or referral by showing those which are most common for other users similar to the user.

In some embodiments, the system may further provide the user with a cost associated with the procedures or drugs prescribed to the similar users. Furthermore, based on the user's geographic location, the system may provide nearby locations which provide the procedures, treatments, or prescription drugs along with comparative costs of each location.

In further embodiments, the system may provide the user with the most probable future outcomes based on the descriptors input by the user and the user information associated with the similar users. The future outcomes may include future diagnoses, procedures, treatments, drugs, and associated costs experienced by the similar users in the future after advancing past the current stage of the user. In some embodiments, the system may determine future outcomes for the next month, year, decade, or the like of the user based on the history of the similar users. In this way, the system allows the user to plan for additional procedures and expenses associated with certain diagnoses, procedures, and treatments which may be difficult to gauge.

FIG. 8B provides a high level process flow for source user information extraction and encoding 801, in accordance with some embodiments of the invention. Specifically, the process flow 801 illustrates the data extraction and encoding processes performed on the source data, described with respect to block 820, previously. These data transformation steps are typically performed by the system 300, via the data extraction device 508 at the respective source server system using the resources of the source server system. As discussed previously and as indicated by Block 822, the system deploys an extraction script on the source data stored at the source server system(s). The script typically comprises computer readable instructions or commands, which when executed (for example, by the source server system, the target system, and the like) cause the source server system, via the data extraction device 508, to selectively extract source data or source user information or other data. The deployed script or command may selectively extract specific data points or datasets from the source server system that are associated with the determined pertinent data for predictive analytics, as described previously. In some embodiments, the system, for example via the extraction script, defines a dataset within a table that is to be delimited, allowing the system to selectively identify and extract specific data points or datasets from the table structure without pulling unnecessary or additional information that is not pertinent. In some embodiments, the script is constructed in T-SQL (Transact-SQL) technical language, for example, to extract data from or interact with the source server system, such as a relational database. In some embodiments, the script is constructed in technical languages such as VB.net, C#, Java script, and the like. In some embodiments, the script is constructed in PL/SQL (Procedural Language/Structured Query Language) technical language. In other embodiments, the script may be constructed in technical languages such as ECL, K, PL/pgSQL, PL/Perl, SQL/PSM, and the like.

In some embodiments, the extraction script is deployed using the processing systems/devices/resources of the associated source server system. Moreover, in some embodiments, the processing systems/devices/resources of the associated source server system are employed to process and export the encoded source data. The source data or source data records of the source server systems may be transformed, formatted, encoded, or otherwise fundamentally altered during the data encoding, delimiting, de-identification and normalization operations performed by the data extraction device 508.

In some embodiments, the system performs normalization of the source data, for example by employing the extraction script. In this regard, normalizing the data may comprise, stripping out/eliminating duplicate data records elements/entries, ordering/organizing/modifying the source data based on the ICD codes, determining and eliminating records with anomalies, and the like. For example, the system may determine that a data record with a patient's age as 999 is inconsistent or an anomaly and discard the data record before further processing at the source itself, thereby eliminating the wastage of technical resources at the system 300. In this regard, some or all of the plurality of technology elements associated with the first record may comprise defective data, and hence may be referred to as defective technology elements. As such, in some instances, normalizing the data may comprise transforming defective data to correct defective data and/or identify and eliminate defective data. The defective data may comprise (i) missing data, (ii) incomplete data, and/or (iii) inconsistent data, and other forms of defects. In some embodiments, defective data may comprise unformatted data, incorrectly formatted data, data redundancies, repetitive entries and the like. The defective data in records may arise due to system errors from the devices/systems or programs that created/augmented the records, inadvertent oversights by personnel creating the records, or lack of availability of/access to pertinent information for the systems/users creating the records. The system 300, and the data extraction device 508, via the script, is configured to transform the extracted source data to correct or eliminate defective data, prior to transmission to the system 300, via the established communication channels.

Next, as illustrated by Block, 824, the system performs de-identification of the source data. In some instances, the de-identification or anonymizing of the source data is performed as a part of the deployed extraction script, while in other instances the de-identification is performed independent of the script, for example, based on transmitting control instructions to the data extraction device 508 to perform the de-identification.

Typically, the source data comprises a plurality of source data records comprising source data/information associated with a plurality of individuals. Typically, each source data record comprises multiple data fields or data elements. Personal identifying information (PII) or sensitive personal information (SPI) is information that can be used on its own or with other information to identify, contact, or locate a person or to identify an individual in context. The multiple data fields of each source data record may comprise a first plurality of data elements comprising user identifying information or PII, such as first name, last name, street address, financial information, and the like. The multiple data fields of each source data record may further comprise a second plurality of data elements comprising user medical and location information, such as physician information, diagnosis, procedure and medication information, state, city, and the like. As discussed previously, the system typically parses and then only extracts at least a portion of the second plurality of data fields without extracting the user identifying information of the first plurality of data elements, to maintain privacy of the individuals. Specifically, de-identifying the source data records comprises constructing a tracer, for each source data record, to generate unique identifiers for the source data record, to facilitate tracking and monitoring of the source data records as they are being encoded into the encoded data file, and/or to facilitate reconstruction of the records once the file is parsed at the target system.

In this regard, the system is configured to identify a first tracer data element and a second tracer data element for each source data record, for example, from the second plurality of data elements. In some embodiments, the first and second tracer data elements may be selected at random for each source data record. In some embodiments, the first and second tracer data elements may be selected based on their contents. For example, the system may identify the first tracer data element as a data field comprising alphanumeric values in its content, or the second tracer data element as a data field having the first four or last six characters as numeric values in its content. In some instances, the first and second tracer data elements are determined for a plurality or set of source data records. For example, the system may determine a zip code data element as the first tracer data element for a set of source data records, or all the data records retrieved from a first source server system. In some instances, the first and second tracer data elements are determined individually for a plurality or set of source data records. For example, the system may determine a pharmacy location data element as the first tracer data element for a first source data record, and the system may determine an ICD code data element as the first tracer data element for another second source data record. In some embodiments, the first tracer data element is the same as the second tracer data element.

Next, the system is configured to parse the records to extract/replicate the contents of the identified first and second tracer data elements, to construct first and second tracer data fields, respectively. In the instances where the first and second tracer data elements are determined for a plurality or set of source data records, the system may then determine, for each record, first and second tracer data fields, comprising contents in the first and second tracer data elements of the record, respectively. For example, the system may determine the first tracer data field of a first source data record of the set of records, to be zip code 1, i.e., the contents of a zip code data element of the first record, while the system may determine the first tracer data field of a second source data record of the set of records, to be zip code 2 based on the contents of the zip code data element. Alternatively, in the instances where the first and second tracer data elements are determined for a plurality or set of source data records, the system may determine common first and second tracer data fields for the records in the set. Continuing with the previous example, the system may determine (for example, at random) the zip code 2 to be the first tracer data field for both the first and second source data record.

In the instances where the first and second tracer data elements are determined individually for a plurality or set of source data records, the system may then determine, for each record, first and second tracer data fields, comprising contents in the first and second tracer data elements of the record, respectively. For example, the system may determine a first tracer data field to be pharmacy location 1 based on contents of the first tracer data element for a first source data record, and the system may determine a first tracer data field to be ICD 2 based on contents of the first tracer data element for another second source data record.

In some embodiments, the system extracts/replicates the contents of the identified first and second tracer data elements, to construct first and second tracer data fields, comprises extracting a predetermined number of characters from a predetermined location from the contents of the data elements. For example, the system may extract the first 5, last 7, or first 3 numeric characters from the contents of a physician address first tracer data element to form the first tracer data field for the record. In the embodiments where the first tracer data element is the same as the second tracer data element, the respective first and second tracer data fields may be same in some instances, while in other instances, they may be distinct (for example, only symbol characters may be extracted for the first tracer data field, while the first 4 characters may be extracted for the second tracer data field).

Next, the system is configured to generate a unique identifier or unique patient (or user) identifier. The unique identifier may comprise a predetermined number and type of characters. In some embodiments, the unique identifier is generated for each record, while in other embodiments, the unique identifier is generated for a set of records or is generated for all the records in a first source data server.

Subsequently, the system constructs a tracer or a tracer element, for each source data record, for uniquely identifying the source data record. Typically, the system appends the first tracer data field with the determined unique identifier, and further appends the result with the second first tracer data field, to construct the tracer. For example, the system may construct a tracer for a first source data record as: "first tracer data field/unique identifier/second first tracer data field." Typically, the novel construction of the tracer ensures that each record of the multitude of records extracted from the plurality of source data servers, is uniquely identified using minimal characters. For example, the construction of the tracer ensures that each record of the multitude of records extracted from the plurality of source data servers has a unique tracer, even if the records of each source data server have the same unique identifier.

Next, as illustrated by block 826, the system performs delimiting of the source data extracted from the source servers to encode the data into an encoded data file. In this regard, the system determines a delimiter (or a plurality of delimiters). The delimiter is a sequence of one or more characters used to specify the boundary between separate, independent data streams, such as between contents of a pair of data elements of a record or a pair of source data records. For example, the delimiter may comprise one or more characters such as, "|", "\", "/*", "<?", and the like. The delimiters may comprise field and record delimiters as described above, bracket delimiters pairs indicating start and end (for example, "<%" and "%>", "/*" and "*/"), and the like. The system may then parse, for each record of the source data records, the data elements (for example, the second plurality of data elements) and extract the contents. Specifically, the system may insert, for each record, the constructed tracer in a encoded data file (such as a text file), followed by a insertion of a delimiter, followed by the contents of the second plurality of data elements, each pair of data elements being separated by a delimiter. The system may then insert a delimiter after the record and further insert the tracer of the subsequent record and the contents of the record in the same manner. In this way, the system constructs the encoded data file comprising encoded source data. Therefore, the system is configured to encode complex data structures (such as relational objects, spreadsheets, and the like) into text in the encoded data file, wherein the encoded data file typically has a significantly smaller file size as alluded to previously.

Subsequently, at block 828, the system transmits the encoded data file to the target server system, via a suitable communication channel, as discussed previously. As discussed previously, for transfer of extracted source data using conventional methods, the file transfer often requires a specific type communication channel that is capable of transferring the large amounts of data (for example, a specific channel having a predetermined bandwidth and throughput capabilities, and estimated file transfer rate for the conventional file size). The initiation of file transfer may be delayed if the required communication channel is unavailable or occupied, and the file transfer through the communication channel itself is often slow due to the large file size. However, the unique data delimiting, de-identification and normalization of the invention and the resulting smaller size of the data file enables the present invention to transfer files through a variety of communication channels and with increased speed. For example, based on determining that a first wireless communication channel with a first bandwidth and file transfer rate is currently busy, the system may route the extracted source data through another second communication channel with a second bandwidth and file transfer rate for the source data, even though the performance parameters of the second channel may be less than/inferior to the parameters of the first channel, which would typically not support file transfer of conventional data extraction. In this regard, the system is configured to switch channels and/or establish new communication channels to reduce wait times, while still enabling the file transfer faster than conventional methods.

Next, at block 829, the system generates a user database at the target server system. Here, the system typically receives the encoded data file at the target server system. The system then parses the encoded data in the encoded data file, and suitably extracts the data, processes the encoded data, to form the processed user information. This processed user information is stored in a structured format in the user database. Typically, the system reconstructs and transforms the encoded data in the encoded data file, into a structured format, based on at least the tracers of the delimiters in the encoded data file. The processing of the user information is described in detail with respect to process flow 800 of FIG. 8A.

FIG. 9 provides a high level process flow for the selective extraction of user information from a source server system 900, in accordance with some embodiments of the invention. As illustrated in block 910 of FIG. 9, the process 900 is initiated by the system establishing an operative communication channel to one or more source server systems as previously described with respect to block 810 of FIG. 8A.

As illustrated in block 920 of the FIG. 9, the systems accesses source data or source user information stored on the one or more source server systems. In some embodiments, the source data or source user information originates from a billing software program or platform such as a billing program utilized by a physician's office or insurance carriers.

The process continues in block 930 of FIG. 9, wherein the system extracts, de-identifies, and delimits the source data or source user information according to extraction criteria, wherein the source data or source user information is transformed into encoded data. In some embodiments, the source data or source user information or data comprises user information from one or more users such as medical records, financial information, and demographic information. The extraction criteria may be a set of predetermined rules used to designate the data of interest to be extracted. For example, a user may wish to only extract information associated with one or more users' gender, age, diagnoses, and received medical procedures. In some embodiments of the invention, the system deploys a script or transmits a command to the source server system to strip the source data or source user information using the decentralized computing resources of the source server system and associated computing devices before the data is extracted. In some embodiments, the system employs the source server system computing resources during a period of time where there is low demand for the computing resources by the source entity, so that the stripping and extracting does not interfere with the source entity's routine processes and tasks.

In some embodiments, de-identifying, delimiting and/or normalizing the source data or source user information further includes stripping the data of anomalies and redundancies before extraction from the source server system. In this way, the system again extracts less information from the source server system and the amount of time required to extract the data is reduced. Anomalies in the data include errors that might incorrectly effect the data. For example, a patient's age might have been incorrectly recorded as 1000 years old. Redundancies in the data may further include repeated data points. Anomalies and redundancies may be detected by imposing limits or rules, such as thresholds, for determining accurate data points. In a non-limiting example, the system may implement a threshold on age, wherein any extracted age 0 and below or 120 and above may flagged or otherwise designated as an anomaly.

In some embodiments of the invention, the process flow further includes de-identifying the user information so that data points cannot be traced back to the personal identity of the patient associated with the data point. While general attributes such as gender, ethnicity, age, and geographical location such as a zip code remain associated with the data point, other specific identifiers such as the patient's name, address, and the like are removed to ensure privacy and anonymity. Additionally, in this way, the amount of data that is transmitted may be further reduced, thereby increasing speed and efficiency of a data pull.

As illustrated in block 940 of FIG. 9, the system selectively extracts the processed user information from the one or more source server systems. By stripping or de-identifying the data before extracting the processed user information from the source server systems, the system reduces the amount of data needed to be transmitted and, therefore, increases the speed of the data extraction process. For example, a user may only need to extract information associated with one or more users' gender, age, diagnoses, and received medical procedures. The system is able to target and designate the specific, desired data and selectively pull the data from the source server system instead of needing to pull the entirety of the database before processing it. Stripping of data prior to selective extraction can reduce data transfer time from a typical several hours or days to mere minutes.

As illustrated in block 950 of FIG. 9, the system generates a user database on a target server system, wherein the database comprises the processed user information selectively extracted from the one or more source server systems.

FIG. 10 provides a high level process flow for the installation of a data extraction device 508 and selective extraction of user information from a source server system 1000, in accordance with some embodiments of the invention. As illustrated in block 1010 of FIG. 10, the process 1000 is initiated by the system installing a data extraction device in one or more source server systems. The data extraction device is a module installed in the source server system which collects and selectively extracts user information from the one or more source server systems in which it is installed. The data extraction device may comprise hardware and/or software installed in the source server system. In some embodiments, the data extraction device may be maintained by a source entity associated with the source server system on which it is installed. In other embodiments, the data extraction device may be maintained by a target entity or third party associated with a system configured to receive extracted user information from the source server system.

As illustrated in block 1020, 1030, and 1040 of the FIG. 10 respectively, the system accesses source data or source user information stored on the one or more source server systems, strips the source data or source user information according to extraction criteria, wherein the source data or source user information is transformed into processed user information, and selectively extracts processed user information from the one or more source server systems as previously discussed with respect to FIG. 9. In some embodiments, the data extraction device performs the data stripping and extraction steps previously discussed. In other embodiments, the data extraction device deploys a script or transmits a command to the source server system to strip the source data or source user information using the decentralized computing resources of the source server system and associated computing devices before the data is selectively extracted.

Finally, as illustrated in block 1050 of FIG. 10, the systems generates a user database on a target server system, wherein the database comprises the processed user information selectively extracted from the one or more source server systems.

It should be understood, that the systems and devices described in FIG. 1, or other devices not specifically described herein, may be configured to establish a communication link with each other in order to accomplish the steps of the processes described herein. The link may be an internal link within the same entity (e.g., within the same financial institution or device provider) or a link with the other systems of entities (e.g., social networking systems, third-party systems, or the like). In some embodiments, the systems may be configured for monitoring the applications and devices that the system(s) utilize as data sources. The information received from monitoring may be provided via wireless network path portions through the Internet. When the systems or devices are not monitoring a source or are not being monitoring, the information need not be transmitted from the source through the Internet to the destination, although it could be. The sources of information may be made continuously available, however, continuously available does not necessarily mean that the sources actually continuously generates data, but that a source is continuously available to generate and send data real-time (e.g., instantaneously and/or within a few seconds, or the like) of receiving a request for it. In any case, the sources may be continuously available to receive and/or generate information, in some cases in digitized data in Internet Protocol (IP) packet format. In response to continuously monitoring the real-time data feeds from the various systems or devices, the system may be configured to provide target information to the user and/or allow the user to make changes to or control the applications and/or devices.

Moreover, it should be understood that the process flows described herein include transforming the information sent and/or received from the applications of the different systems (e.g., internally or externally) and/or the devices from one or more data formats into a data format associated with an application for display to the user on the user device. There are many ways in which information is converted within the system environment. This may be seamless, as in the case of upgrading to a newer version of a computer program. Alternatively, the conversion may require processing by the use of a special conversion program, or it may involve a complex process of going through intermediary stages, or involving complex "exporting" and "importing" procedures, which may convert to and from a tab-delimited or comma-separated text file. In some cases, a program may recognize several data file formats at the data input stage and then is also capable of storing the output data in a number of different formats. Such a program may be used to convert a file format. If the source format or target format is not recognized, then at times a third program may be available which permits the conversion to an intermediate format, which can then be reformatted.

As will be appreciated by one of skill in the art, the present invention may be embodied as a method (including, for example, a computer-implemented process, a business process, and/or any other process), apparatus (including, for example, a system, machine, device, computer program product, and/or the like), or a combination of the foregoing. Accordingly, embodiments of the present invention may take the form of an entirely hardware embodiment, an entirely software embodiment (including firmware, resident software, micro-code, etc.), or an embodiment combining software and hardware aspects that may generally be referred to herein as a "system." Furthermore, embodiments of the present invention may take the form of a computer program product on a computer-readable medium having computer-executable program code embodied in the medium.

Any suitable transitory or non-transitory computer readable medium may be utilized. The computer readable medium may be, for example but not limited to, an electronic, magnetic, optical, electromagnetic, infrared, or semiconductor system, apparatus, or device. More specific examples of the computer readable medium include, but are not limited to, the following: an electrical connection having one or more wires; a tangible storage medium such as a portable computer diskette, a hard disk, a random access memory (RAM), a read-only memory (ROM), an erasable programmable read-only memory (EPROM or Flash memory), a compact disc read-only memory (CD-ROM), or other optical or magnetic storage device.

In the context of this document, a computer readable medium may be any medium that can contain, store, communicate, or transport the program for use by or in connection with the instruction execution system, apparatus, or device. The computer usable program code may be transmitted using any appropriate medium, including but not limited to the Internet, wireline, optical fiber cable, radio frequency (RF) signals, or other mediums.

Computer-executable program code for carrying out operations of embodiments of the present invention may be written in an object oriented, scripted or unscripted programming language such as Java, VB.net, C#, TSQL, Perl, Smalltalk, C++, and/or the like. However, the computer program code for carrying out operations of embodiments of the present invention may also be written in conventional procedural programming languages, such as the "C" programming language or similar programming languages.

Embodiments of the present invention are described above with reference to flowchart illustrations and/or block diagrams of methods, apparatus (systems), and computer program products. It will be understood that each block of the flowchart illustrations and/or block diagrams, and/or combinations of blocks in the flowchart illustrations and/or block diagrams, can be implemented by computer-executable program code portions. These computer-executable program code portions may be provided to a processor of a general purpose computer, special purpose computer, or other programmable data processing apparatus to produce a particular machine, such that the code portions, which execute via the processor of the computer or other programmable data processing apparatus, create mechanisms for implementing the functions/acts specified in the flowchart and/or block diagram block or blocks.

These computer-executable program code portions may also be stored in a computer-readable memory that can direct a computer or other programmable data processing apparatus to function in a particular manner, such that the code portions stored in the computer readable memory produce an article of manufacture including instruction mechanisms which implement the function/act specified in the flowchart and/or block diagram block(s).

The computer-executable program code may also be loaded onto a computer or other programmable data processing apparatus to cause a series of operational steps to be performed on the computer or other programmable apparatus to produce a computer-implemented process such that the code portions which execute on the computer or other programmable apparatus provide steps for implementing the functions/acts specified in the flowchart and/or block diagram block(s). Alternatively, computer program implemented steps or acts may be combined with operator or human implemented steps or acts in order to carry out an embodiment of the invention.

Embodiments of the present invention are described above with reference to flowcharts and/or block diagrams. It will be understood that steps of the processes described herein may be performed in orders different than those illustrated in the flowcharts. In other words, the processes represented by the blocks of a flowchart may, in some embodiments, be in performed in an order other that the order illustrated, may be combined or divided, or may be performed simultaneously. It will also be understood that the blocks of the block diagrams illustrated, in some embodiments, merely conceptual delineations between systems and one or more of the systems illustrated by a block in the block diagrams may be combined or share hardware and/or software with another one or more of the systems illustrated by a block in the block diagrams. Likewise, a device, system, apparatus, and/or the like may be made up of one or more devices, systems, apparatuses, and/or the like. For example, where a processor is illustrated or described herein, the processor may be made up of a plurality of microprocessors or other processing devices which may or may not be coupled to one another. Likewise, where a memory is illustrated or described herein, the memory may be made up of a plurality of memory devices which may or may not be coupled to one another.

While certain exemplary embodiments have been described and shown in the accompanying drawings, it is to be understood that such embodiments are merely illustrative of, and not restrictive on, the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

What is claimed is:

1. A system for resource-efficient extraction and optimized transmission of medical data for a medical diagnostic platform, wherein the system is structured for selectively extracting, normalizing and delimiting data by stripping out identifying information while still securely correlating of users' medical data for predictive diagnostic analysis with increased accuracy the system comprising:
   at least one memory device with computer-readable program code stored thereon;
   at least one communication device connected to a network;
   at least one processing device operatively coupled to the at least one memory device and the at least one communication device, wherein the processing device is configured to execute the computer-readable program code to:
      establish an operative communication channel with a source server system, the source server system comprising source data and source user information, wherein the source data and source user information comprises medical record data and identifying information associated with a plurality of users, wherein establishing the operative communication channel further comprises:
         transmitting, via the operative communication channel, a data extraction device to the source server system; and
         storing the data extraction device on a memory device of the source server system, wherein upon execution the data extraction device is structured to selectively extract data from the source server system via one or more resources of the source server system;

identify a modified portion of the source data and the source user information from a previous extraction;

determine, via the data extraction device at the source server system, whether the source server system comprises one or more underutilized computing resources of the source server system, wherein the one or more underutilized computing resources comprise idle processing resources, memory resources, and/or communication portals;

based on (i) determining that source server system currently comprises one or more underutilized computing resources, and/or (ii) determining that source server system comprises one or more underutilized computing resources associated with a predetermined idle time, extract, via the data extraction device and the one or more underutilized computing resources at the source server system, selectively, the modified portion of the source data and the source user information from the source server system to a target server system, wherein the selectively extracting portion of the source data and source user information comprises de-identifying data by not extracting the identifying information of the source data and source user information associated with a plurality of users, wherein the portion of the source data and the source user information comprises the medical data associated with the plurality of users of a first file size, wherein extracting further comprises:

generating an encoded data file having a second file size from the portion of the source data and the source user information, wherein the second file size is less than the first file size; and identifying a first communication channel associated with the source server system having one or more first performance parameters; and in response to determining that the first communication channel is busy, transmitting the encoded data file to the target server system via a second communication channel associated with the source server system having one or more second performance parameters, wherein the one or more second performance parameters are lower than the one or more first performance parameters; and generate a user database on the target server system, wherein the user database comprises the anonymized portion of the source data and the source user information selectively extracted from the source server system.

2. The system of claim 1, wherein the data extraction device comprises an extraction script that utilizes computing resources of the source server system to preprocess and selectively extract the portion of the source data and the source user information at a predetermined time, wherein preprocessing comprises normalizing, de-identifying, and delimiting the modified portion of the source data and the source user information at the source server system.

3. The system of claim 1, wherein the at least one processing device is further configured to:

determine a first time period associated with completion of extraction of the modified portion of the source data and the source user information from the source server system to the target server system;

determine a duration of availability associated with the one or more underutilized computing resources at the source server system; and wherein extracting the modified portion of the source data and the source user information, further comprises, extracting the modified portion of the source data and the source user information, via the data extraction device and the one or more underutilized computing resources at the source server system, in response to determining that the first time period associated with completion of extraction occurs within the duration of availability of the one or more underutilized computing resources.

4. The system of claim 3, wherein the one or more underutilized computing resources of the source server system further comprise a plurality of decentralized computing resources of one or more computing devices associated with the source server system.

5. The system of claim 1, wherein preprocessing the portion of the source data and the source user information on the source server system the system normalizes, delimits, and de-identifies the data using unused computing resources of the source server system prior to extraction of the data from the source server system.

6. The system of claim 1, wherein the encoded data file is associated with a text file type;

wherein the one or more first performance parameters of the first communication channel are compatible with transmissions of the first file size, wherein the one or more first performance parameters comprise bandwidth, throughput, and file transfer rate; and wherein the one or more second performance parameters of the second communication channel are not compatible with transmissions of the first file size, wherein the one or more second performance parameters comprise bandwidth, throughput, and file transfer rate.

7. The system of claim 1, wherein selectively extracting the portion of the source data and the source user information further comprises:

receiving at least one data descriptor input from a user interface, wherein the data descriptor comprises a diagnosis, symptom, procedure, treatment, ICD code, age range, gender, geographic location, ethnicity, and/or medical procedure associated with predictive diagnosis of a first user;

based on the at least one data descriptor, identifying pertinent data for extraction from the portion of the source data and the source user information associated with the plurality of users, wherein the identified pertinent data from extraction is associated with only one or more similar users of the plurality of users that match the data descriptor associated with the first user;

stripping the portion of the source data and the source user information based on the at least one data descriptor to construct a pertinent data file, the pertinent data file comprising only the pertinent data;

extracting the pertinent data file from the source server system; and generating a predictive analysis interface comprising predictive results for the first user based on the pertinent data file, wherein the predictive results comprise a predicted future diagnosis, medical treatment, medical procedure, and/or medical cost for the first user determined based on the source data and the source user information associated with the one or more similar users of the plurality of users.

8. The system of claim 1, wherein the processing device is further configured to execute the computer-readable program code to:
- receive at least one data descriptor input from a user interface for a first user, wherein the data descriptor comprises a diagnosis, symptom, procedure, treatment, age range, gender, geographic location, ethnicity, and/or medical procedure associated with predictive diagnosis of the first user;
- based on the at least one data descriptor, identifying one or more similar users of the plurality of users associated with the anonymized source data and source user information at the user database that match the data descriptor associated with the first user; and
- generating a predictive analysis interface comprising predictive results for the first user based on the one or more similar users, wherein the predictive results comprise a predicted future diagnosis, medical treatment, medical procedure, and/or medical cost for the first user determined based on the anonymized source data and source user information associated with the one or more similar users of the plurality of users.

9. The system of claim 8, wherein the processing device is further configured to execute the computer-readable program code to generate an ICD code based on the at least one data descriptor associated with the first user, wherein identifying one or more similar users of the plurality of users further comprises:
- constructing a plurality of filters associated with the at least one data descriptor, and
- stacking the plurality of filters over the anonymized source data and source user information at the user database such that each of the stacked plurality of filters sequentially provide decreasing subset sizes of results.

10. The system of claim 8, wherein the predictive analysis interface associated with the first user, further comprises a comparison of a first diagnosis provided by the first user and diagnoses associated the one or more similar users.

11. A computer-implemented method for resource-efficient processing and selective extraction of medical data for a medical diagnostic platform, wherein the method is structured for selectively extracting, normalizing and delimiting data by stripping out identifying information while still securely correlating of users' medical data for predictive diagnostic analysis with increased accuracy, the method comprising:
- establishing an operative communication channel with a source server system comprising source data and source user information, wherein the source data and source user information comprises medical record data and identifying information associated with a plurality of users, wherein establishing the operative communication channel further comprises:
  - transmitting, via the operative communication channel, a data extraction device to the source server system; and
  - storing the data extraction device on a memory device of the source server system, wherein upon execution the data extraction device is structured to selectively extract data from the source server system via one or more resources of the source server system;
- identifying a modified portion of the source data and the source user information from a previous extraction;
- determining, via the data extraction device at the source server system, whether the source server system comprises one or more underutilized computing resources of the source server system, wherein the one or more underutilized computing resources comprise idle processing resources, memory resources, and/or communication portals;
- based on (i) determining that source server system currently comprises one or more underutilized computing resources, and/or (ii) determining that source server system comprises one or more underutilized computing resources associated with a predetermined idle time, extracting, via the data extraction device and the one or more underutilized computing resources at the source server system, selectively, the modified portion of the source data and the source user information from the source server system to a target server system, wherein the selectively extracting portion of the source data and source user information comprises de-identifying data by not extracting the identifying information of the source data and source user information associated with a plurality of users, wherein the portion of the source data and the source user information comprises the medical data associated with the plurality of users of a first file size, wherein extracting further comprises:
  - generating an encoded data file having a second file size from the portion of the source data and the source user information, wherein the second file size is less than the first file size; and
  - identifying a first communication channel associated with the source server system having one or more first performance parameters; and
  - in response to determining that the first communication channel is busy, transmitting the encoded data file to the target server system via a second communication channel associated with the source server system having one or more second performance parameters, wherein the one or more second performance parameters are lower than the one or more first performance parameters; and
- generating a user database on the target server system, wherein the user database comprises the anonymized portion of the source data and the source user information extracted from the source server system.

12. The computer-implemented method of claim 11, wherein normalizing the portion of the source data and the source user information further comprises:
- identifying one or more anomalies and redundancies in the portion of the source data and the source user information, wherein the one or more anomalies and redundancies comprise missing data, incomplete data, inconsistent data, incorrect data, unformatted data, and repeated data entries; and
- based on identifying the one or more anomalies and redundancies, stripping the one or more anomalies and redundancies from the portion of the source data and the source user information prior to extraction.

13. The computer-implemented method of claim 11, wherein de-identifying the portion of the source data and the source user information further comprises:
- identifying at least some personal identifying information within the portion of the source data and the source user information; and
- based on identifying the at least some personal identifying information, stripping the portion of the source data and the source user information of the personal identifying information to generate de-identified data.

14. The computer-implemented method of claim 13, wherein generating the de-identified data further comprises constructing at least one tracer for each de-identified data record, wherein the at least one tracer is a unique identifier for the de-identified data record configured for tracking and monitoring of the de-identified data record during data extraction, and wherein the at least one tracer is used for reconstruction of the portion of the source data and the source user information at the target server system.

15. The computer-implemented method of claim 14, wherein delimiting the modified portion of the source data and the source user information further comprises:
generating encoded source data by inserting the at least one tracer into the portion of the source data and the source user information; and
generating the encoded data file comprising the encoded source data.

16. The computer-implemented method of claim 15, wherein generating the encoded source data further comprises inserting a delimiter into the encoded source data with the tracer and the portion of the source data and the source user information.

17. The computer-implemented method of claim 11, wherein selectively extracting the portion of the source data and the source user information further comprises:
receiving at least one data descriptor input from a user interface, wherein the data descriptor comprises a diagnosis, symptom, procedure, treatment, ICD code, age range, gender, geographic location, ethnicity, and/or medical procedure associated with predictive diagnosis of a first user;
based on the at least one data descriptor, identifying pertinent data for extraction from the portion of the source data and the source user information associated with the plurality of users, wherein the identified pertinent data from extraction is associated with only one or more similar users of the plurality of users that match the data descriptor associated with the first user;
stripping the portion of the source data and the source user information based on the at least one data descriptor, wherein a pertinent data file comprising only the pertinent data is created;
selectively extracting the pertinent data file from the source server system; and
generating a predictive analysis interface comprising predictive results for the first user based on the pertinent data file, wherein the predictive results comprise a predicted future diagnosis, medical treatment, medical procedure, and/or medical cost for the first user determined based on the source data and the source user information associated with the one or more similar users of the plurality of users.

18. A medical diagnostic platform comprising a computer program product having at least one non-transitory computer-readable medium having computer-readable program code portions embodied therein, wherein the computer program product is structured for selectively extracting, normalizing and delimiting data by stripping out identifying information while still securely correlating of users' medical data for predictive diagnostic analysis with increased accuracy, the computer-readable program code portions comprising executable portions for:
establishing an operative communication channel with a source server system comprising source data and source user information, wherein the source data and source user information comprises medical record data and identifying information associated with a plurality of users, wherein establishing the operative communication channel further comprises:
transmitting, via the operative communication channel, a data extraction device to the source server system; and
storing the data extraction device on a memory device of the source server system, wherein upon execution the data extraction device is structured to selectively extract data from the source server system via one or more resources of the source server system;
identifying a modified portion of the source data and the source user information from a previous extraction;
determining, via the data extraction device at the source server system, whether the source server system comprises one or more underutilized computing resources of the source server system, wherein the one or more underutilized computing resources comprise idle processing resources, memory resources, and/or communication portals;
based on (i) determining that source server system currently comprises one or more underutilized computing resources, and/or (ii) determining that source server system comprises one or more underutilized computing resources associated with a predetermined idle time, extracting, via the data extraction device and the one or more underutilized computing resources at the source server system, selectively, the modified portion of the source data and the source user information from the source server system to a target server system, wherein the selectively extracting portion of the source data and source user information comprises de-identifying data by not extracting the identifying information of the source data and source user information associated with a plurality of users, wherein the portion of the source data and the source user information comprises the medical data associated with the plurality of users of a first file size, wherein extracting further comprises:
generating an encoded data file having a second file size from the portion of the source data and the source user information, wherein the second file size is less than the first file size; and
identifying a first communication channel associated with the source server system having one or more first performance parameters; and
in response to determining that the first communication channel is busy, transmitting the encoded data file to the target server system via a second communication channel associated with the source server system having one or more second performance parameters, wherein the one or more second performance parameters are lower than the one or more first performance parameters;
generating a centralized user database, wherein the centralized user database comprises anonymized user data selectively extracted from a plurality of source server systems via one or more operative communication channels;
receiving, via a user interface, at least one descriptor from a user;
based on the at least one descriptor received from the user, matching the user to one or more similar users associated with the anonymized user data;
retrieving tailored data from the centralized user database associated with the one or more similar users; and
generating a medical diagnostic report comprising the tailored data, wherein the medical diagnostic report is presented to the user via the user interface.

19. The medical diagnostic platform of claim 18, wherein the medical diagnostic report comprises at least one of extrapolated diagnoses, treatments, procedures, and costs associated with the user based on the similar users and the anonymized user data.

20. The medical diagnostic platform of claim 18, wherein the at least one descriptor is selected from a group comprising age, gender, ethnicity, geographic location, income, diagnoses, symptoms, procedures, treatments, and drug prescriptions associated with the user or the similar users.

* * * * *